US011135454B2

(12) United States Patent
Xu et al.

(10) Patent No.: US 11,135,454 B2
(45) Date of Patent: Oct. 5, 2021

(54) HISTOTRIPSY THERAPY SYSTEMS AND METHODS FOR THE TREATMENT OF BRAIN TISSUE (71) Applicant: THE REGENTS OF THE UNIVERSITY OF MICHIGAN, Ann Arbor, MI (US)

(72) Inventors: Zhen Xu, Ann Arbor, MI (US); Jonathan Sukovich, Ann Arbor, MI (US); Aditya S. Pandey, Ann Arbor, MI (US); Charles A. Cain, Ann Arbor, MI (US); Hitinder S. Gurm, Ann Arbor, MI (US)

(73) Assignee: THE REGENTS OF THE UNIVERSITY OF MICHIGAN, Ann Arbor, MI (US)

(*) Notice: Subject to any disclaimer, the term of this patent is extended or adjusted under 35 U.S.C. 154(b) by 184 days.

(21) Appl. No.: 15/737,761

(22) PCT Filed: Jun. 23, 2016

(86) PCT No.: PCT/US2016/039020
§ 371 (c)(1),
(2) Date: Dec. 19, 2017

(87) PCT Pub. No.: WO2016/210133
PCT Pub. Date: Dec. 29, 2016

(65) Prior Publication Data
US 2018/0154186 A1 Jun. 7, 2018

Related U.S. Application Data (60) Provisional application No. 62/184,179, filed on Jun. 24, 2015.

(51) Int. Cl.
*A61N 7/02* (2006.01)
*A61N 7/00* (2006.01)

(52) U.S. Cl.
CPC ............ *A61N 7/02* (2013.01); *A61N 7/00* (2013.01); *A61N 2007/003* (2013.01);
(Continued)

(58) Field of Classification Search
CPC ...... A61N 2007/003; A61N 2007/0039; A61N 2007/0047; A61N 2007/0065;
(Continued)

(56) References Cited

U.S. PATENT DOCUMENTS 3,243,497 A 3/1966 Kendall et al.
3,679,021 A 7/1972 Goldberg et al.
(Continued)

FOREIGN PATENT DOCUMENTS

CN 1669672 A 9/2005
CN 1732031 A 2/2006
(Continued)

OTHER PUBLICATIONS

Bak; Rapid protytyping or rapid production? 3D printing processes move industry towards the latter; Assembly Automation; 23(4); pp. 340-345; Dec. 1, 2003.
(Continued)

*Primary Examiner* — Joanne M Hoffman
*Assistant Examiner* — Alexei Bykhovski
(74) *Attorney, Agent, or Firm* — Shay Glenn LLP (57) ABSTRACT A histotripsy therapy system configured for the treatment of brain tissue is provided, which may include any number of features. In one embodiment, the system includes an ultrasound therapy transducer, a drainage catheter, and a plurality of piezoelectric sensors disposed in the drainage catheter. The ultrasound therapy is configured to transmit ultrasound pulses into the brain to generate cavitation that liquefies a target tissue in the brain. The drainage catheter is configured to detect the ultrasound pulses. An aberration correction
(Continued)

algorithm can be executed by the system based on the ultrasound pulses measured by the drainage catheter to automatically correct for an aberration effect caused by the ultrasound pulses passing through a skullcap of the patient.

17 Claims, 5 Drawing Sheets

(52) U.S. Cl.
    CPC .............. *A61N 2007/0039* (2013.01); *A61N 2007/0047* (2013.01); *A61N 2007/0065* (2013.01); *A61N 2007/0078* (2013.01); *A61N 2007/0086* (2013.01); *A61N 2007/0095* (2013.01)

(58) Field of Classification Search
    CPC .... A61N 2007/0078; A61N 2007/0086; A61N 2007/0095; A61N 7/00; A61N 7/02
    See application file for complete search history.

(56) References Cited

U.S. PATENT DOCUMENTS

| | | |
|---|---|---|
| 3,879,699 A | 4/1975 | Pepper |
| 4,016,749 A | 4/1977 | Wachter |
| 4,024,501 A | 5/1977 | Herring et al. |
| 4,051,394 A | 9/1977 | Tieden |
| 4,117,446 A | 9/1978 | Alais |
| 4,266,747 A | 5/1981 | Souder, Jr. et al. |
| 4,269,174 A | 5/1981 | Adair |
| 4,277,367 A | 7/1981 | Madsen et al. |
| 4,351,038 A | 9/1982 | Alais |
| 4,406,153 A | 9/1983 | Ophir et al. |
| 4,440,025 A | 4/1984 | Hayakawa et al. |
| 4,447,031 A | 5/1984 | Souder, Jr. et al. |
| 4,453,408 A | 6/1984 | Clayman |
| 4,483,345 A | 11/1984 | Miwa |
| 4,548,374 A | 10/1985 | Thompson et al. |
| 4,549,533 A | 10/1985 | Cain et al. |
| 4,550,606 A | 11/1985 | Drost |
| 4,551,794 A | 11/1985 | Sandell |
| 4,575,330 A | 3/1986 | Hull |
| 4,622,972 A | 11/1986 | Giebeler, Jr. |
| 4,625,731 A | 12/1986 | Quedens et al. |
| 4,641,378 A | 2/1987 | McConnell et al. |
| 4,669,483 A | 6/1987 | Hepp et al. |
| 4,689,986 A | 9/1987 | Carson et al. |
| 4,757,820 A | 7/1988 | Itoh |
| 4,791,915 A | 12/1988 | Barsotti et al. |
| 4,819,621 A | 4/1989 | Ueberle et al. |
| 4,829,491 A | 5/1989 | Saugeon et al. |
| 4,856,107 A | 8/1989 | Dory |
| 4,865,042 A | 9/1989 | Umemura et al. |
| 4,888,746 A | 12/1989 | Wurster et al. |
| 4,890,267 A | 12/1989 | Rudolph |
| 4,922,917 A | 5/1990 | Dory |
| 4,938,217 A | 7/1990 | Lele |
| 4,957,099 A | 9/1990 | Hassler |
| 4,973,980 A | 11/1990 | Howkins et al. |
| 4,984,575 A | 1/1991 | Uchiyama et al. |
| 4,991,151 A | 2/1991 | Dory |
| 4,995,012 A | 2/1991 | Dory |
| RE33,590 E | 5/1991 | Dory |
| 5,014,686 A | 5/1991 | Schafer |
| 5,065,751 A | 11/1991 | Wolf |
| 5,080,101 A | 1/1992 | Dory |
| 5,080,102 A | 1/1992 | Dory |
| 5,091,893 A | 2/1992 | Smith et al. |
| 5,092,336 A | 3/1992 | Fink |
| 5,097,709 A | 3/1992 | Masuzawa et al. |
| 5,111,822 A | 5/1992 | Dory |
| 5,143,073 A | 9/1992 | Dory |
| 5,143,074 A | 9/1992 | Dory |
| 5,150,711 A | 9/1992 | Dory |
| 5,158,070 A | 10/1992 | Dory |
| 5,158,071 A | 10/1992 | Umemura et al. |
| 5,163,421 A | 11/1992 | Bernstein et al. |
| 5,165,412 A | 11/1992 | Okazaki |
| 5,174,294 A | 12/1992 | Saito et al. |
| 5,209,221 A | 5/1993 | Riedlinger |
| 5,215,680 A | 6/1993 | D'Arrigo |
| 5,219,401 A | 6/1993 | Cathignol et al. |
| 5,222,806 A | 6/1993 | Roberts |
| 5,230,340 A | 7/1993 | Rhyne |
| 5,295,484 A | 3/1994 | Marcus et al. |
| 5,316,000 A | 5/1994 | Chapelon et al. |
| 5,354,258 A | 10/1994 | Dory |
| 5,380,411 A | 1/1995 | Schlief |
| 5,393,296 A | 2/1995 | Rattner |
| 5,409,002 A | 4/1995 | Pell |
| 5,431,621 A | 7/1995 | Dory |
| 5,435,311 A | 7/1995 | Umemura et al. |
| 5,443,069 A | 8/1995 | Schaetzle |
| 5,450,305 A | 9/1995 | Boys et al. |
| 5,469,852 A | 11/1995 | Nakamura et al. |
| 5,474,071 A | 12/1995 | Chapelon et al. |
| 5,474,531 A | 12/1995 | Carter |
| 5,490,051 A | 2/1996 | Messana |
| 5,501,655 A | 3/1996 | Rolt et al. |
| 5,520,188 A | 5/1996 | Hennige et al. |
| 5,523,058 A | 6/1996 | Umemura et al. |
| 5,524,620 A | 6/1996 | Rosenschein |
| 5,540,909 A | 7/1996 | Schutt |
| 5,542,935 A | 8/1996 | Unger et al. |
| 5,558,092 A | 9/1996 | Unger et al. |
| 5,563,346 A | 10/1996 | Bartelt et al. |
| 5,566,675 A | 10/1996 | Li et al. |
| 5,573,497 A | 11/1996 | Chapelon |
| 5,580,575 A | 12/1996 | Unger et al. |
| 5,582,578 A | 12/1996 | Zhong et al. |
| 5,590,657 A | 1/1997 | Cain et al. |
| 5,601,526 A | 2/1997 | Chapelon et al. |
| 5,617,862 A | 4/1997 | Cole et al. |
| 5,648,098 A | 7/1997 | Porter |
| 5,666,954 A | 9/1997 | Chapelon et al. |
| 5,676,452 A | 10/1997 | Scholz |
| 5,676,692 A | 10/1997 | Sanghvi et al. |
| 5,678,554 A | 10/1997 | Hossack et al. |
| 5,694,936 A | 12/1997 | Fujimoto et al. |
| 5,695,460 A | 12/1997 | Siegel et al. |
| 5,717,657 A | 2/1998 | Ruffa |
| 5,724,972 A | 3/1998 | Petrofsky |
| 5,743,863 A | 4/1998 | Chapelon |
| 5,753,929 A | 5/1998 | Bliss |
| 5,759,162 A | 6/1998 | Oppelt et al. |
| 5,766,138 A | 6/1998 | Rattner |
| 5,769,790 A | 6/1998 | Watkins et al. |
| 5,797,848 A | 8/1998 | Marian et al. |
| 5,820,623 A | 10/1998 | Ng |
| 5,823,962 A | 10/1998 | Schaetzle et al. |
| 5,827,204 A | 10/1998 | Grandia et al. |
| 5,836,896 A | 11/1998 | Rosenschein |
| 5,849,727 A | 12/1998 | Porter et al. |
| 5,873,902 A | 2/1999 | Sanghvi et al. |
| 5,879,314 A | 3/1999 | Peterson et al. |
| 5,932,807 A | 8/1999 | Mallart |
| 5,947,904 A | 9/1999 | Hossack et al. |
| 6,001,069 A | 12/1999 | Tachibana et al. |
| 6,022,309 A | 2/2000 | Celliers et al. |
| 6,036,667 A | 3/2000 | Manna et al. |
| 6,088,613 A | 7/2000 | Unger |
| 6,093,883 A | 7/2000 | Sanghvi et al. |
| 6,113,558 A | 9/2000 | Rosenschein et al. |
| 6,126,607 A | 10/2000 | Whitmore, III et al. |
| 6,128,958 A | 10/2000 | Cain |
| 6,143,018 A | 11/2000 | Beuthan et al. |
| 6,165,144 A | 12/2000 | Talish et al. |
| 6,176,842 B1 | 1/2001 | Tachibana et al. |
| 6,296,619 B1 | 10/2001 | Brisken et al. |
| 6,308,585 B1 | 10/2001 | Nilsson et al. |
| 6,308,710 B1 | 10/2001 | Silva |
| 6,309,355 B1 | 10/2001 | Cain et al. |

(56) References Cited

U.S. PATENT DOCUMENTS

| | | |
|---|---|---|
| 6,318,146 B1 | 11/2001 | Madsen et al. |
| 6,321,109 B2 | 11/2001 | Ben-Haim et al. |
| 6,338,566 B1 | 1/2002 | Verdier |
| 6,344,489 B1 | 2/2002 | Spears |
| 6,391,020 B1 | 5/2002 | Kurtz et al. |
| 6,413,216 B1 | 7/2002 | Cain et al. |
| 6,419,648 B1 | 7/2002 | Vitek et al. |
| 6,470,204 B1 | 10/2002 | Uzgiris et al. |
| 6,488,639 B1 | 12/2002 | Ribault et al. |
| 6,490,469 B2 | 12/2002 | Candy |
| 6,500,141 B1 | 12/2002 | Irion et al. |
| 6,506,154 B1 | 1/2003 | Ezion et al. |
| 6,506,171 B1 | 1/2003 | Vitek et al. |
| 6,508,774 B1 | 1/2003 | Acker et al. |
| 6,511,428 B1 | 1/2003 | Azuma et al. |
| 6,511,444 B2 | 1/2003 | Hynynen et al. |
| 6,522,142 B1 | 2/2003 | Freundlich |
| 6,524,251 B2 | 2/2003 | Rabiner et al. |
| 6,536,553 B1 | 3/2003 | Scanlon |
| 6,543,272 B1 | 4/2003 | Vitek |
| 6,556,750 B2 | 4/2003 | Constantino et al. |
| 6,559,644 B2 | 5/2003 | Froundlich et al. |
| 6,576,220 B2 | 6/2003 | Unger |
| 6,599,288 B2 | 7/2003 | Maguire et al. |
| 6,607,498 B2 | 8/2003 | Eshel |
| 6,612,988 B2 | 9/2003 | Maor et al. |
| 6,613,004 B1 | 9/2003 | Vitek et al. |
| 6,613,005 B1 | 9/2003 | Friedman et al. |
| 6,626,854 B2 | 9/2003 | Friedman et al. |
| 6,626,855 B1 | 9/2003 | Weng et al. |
| 6,645,162 B2 | 11/2003 | Friedman et al. |
| 6,648,839 B2 | 11/2003 | Manna et al. |
| 6,666,833 B1 | 12/2003 | Friedman et al. |
| 6,685,640 B1 | 2/2004 | Fry et al. |
| 6,685,657 B2 | 2/2004 | Jones |
| 6,705,994 B2 | 3/2004 | Vortman et al. |
| 6,719,449 B1 | 4/2004 | Laugharn, Jr. et al. |
| 6,719,694 B2 | 4/2004 | Weng et al. |
| 6,735,461 B2 | 5/2004 | Vitek et al. |
| 6,736,814 B2 | 5/2004 | Manna et al. |
| 6,750,463 B1 | 6/2004 | Riley |
| 6,770,031 B2 | 8/2004 | Hynynen et al. |
| 6,775,438 B1 | 8/2004 | Gaedke et al. |
| 6,788,977 B2 | 9/2004 | Fenn et al. |
| 6,790,180 B2 | 9/2004 | Vitek |
| 6,820,160 B1 | 11/2004 | Allman |
| 6,852,082 B2 | 2/2005 | Strickberger et al. |
| 6,869,439 B2 | 3/2005 | White et al. |
| 6,890,332 B2 | 5/2005 | Truckai et al. |
| 6,929,609 B2 | 8/2005 | Asafusa |
| 7,004,282 B2 | 2/2006 | Manna et al. |
| 7,059,168 B2 | 6/2006 | Hibi et al. |
| 7,128,711 B2 | 10/2006 | Medan et al. |
| 7,128,719 B2 | 10/2006 | Rosenberg |
| 7,175,596 B2 | 2/2007 | Vitek et al. |
| 7,196,313 B2 | 3/2007 | Quinones |
| 7,223,239 B2 | 5/2007 | Schulze et al. |
| 7,258,674 B2 | 8/2007 | Cribbs et al. |
| 7,273,458 B2 | 9/2007 | Prausnitz et al. |
| 7,273,459 B2 | 9/2007 | Desilets et al. |
| 7,300,414 B1 | 11/2007 | Holland et al. |
| 7,311,679 B2 | 12/2007 | Desilets et al. |
| 7,331,951 B2 | 2/2008 | Eshel et al. |
| 7,341,569 B2 | 3/2008 | Soltani et al. |
| 7,347,855 B2 | 3/2008 | Eshel et al. |
| 7,358,226 B2 | 4/2008 | Dayton et al. |
| 7,359,640 B2 | 4/2008 | Onde et al. |
| 7,367,948 B2 | 5/2008 | O'Donnell et al. |
| 7,374,551 B2 | 5/2008 | Liang et al. |
| 7,377,900 B2 | 5/2008 | Vitek et al. |
| 7,429,249 B1 | 9/2008 | Winder et al. |
| 7,431,704 B2 | 10/2008 | Babaev |
| 7,442,168 B2 | 10/2008 | Novak et al. |
| 7,462,488 B2 | 12/2008 | Madsen et al. |
| 7,559,905 B2 | 7/2009 | Kagosaki et al. |
| 7,656,638 B2 | 2/2010 | Laakso et al. |
| 7,695,437 B2 | 4/2010 | Quistgaard et al. |
| 7,714,481 B2 | 5/2010 | Sakai |
| 7,771,359 B2 | 8/2010 | Adam |
| 7,967,763 B2 | 6/2011 | Deem et al. |
| 8,057,408 B2 | 11/2011 | Cain et al. |
| 8,295,912 B2 | 10/2012 | Gertner |
| 8,333,115 B1 | 12/2012 | Garvey et al. |
| 8,337,407 B2 | 12/2012 | Quistgaard et al. |
| 8,342,467 B2 | 1/2013 | Stachowski et al. |
| 8,376,970 B2 | 2/2013 | Babaev |
| 8,539,813 B2 | 9/2013 | Cain et al. |
| 8,568,339 B2 | 10/2013 | Rybyanets |
| 8,636,664 B2 | 1/2014 | Brannan |
| 8,715,187 B2 | 5/2014 | Landberg Davis et al. |
| 8,845,537 B2 | 9/2014 | Tanaka et al. |
| 8,932,239 B2 | 1/2015 | Sokka et al. |
| 9,028,434 B2 | 5/2015 | Tanaka |
| 9,049,783 B2 | 6/2015 | Teofilovic |
| 9,061,131 B2 | 6/2015 | Jahnke et al. |
| 9,144,694 B2 | 9/2015 | Cain |
| 9,220,476 B2 | 12/2015 | Coussios et al. |
| 9,228,730 B1 | 1/2016 | Inbody |
| 9,302,124 B2 | 4/2016 | Konofagou et al. |
| 9,457,201 B2 | 10/2016 | Hoelscher et al. |
| 9,526,923 B2 | 12/2016 | Jahnke et al. |
| 9,636,133 B2 | 5/2017 | Hall et al. |
| 9,642,634 B2 | 5/2017 | Cain et al. |
| 9,763,688 B2 | 9/2017 | Stulen et al. |
| 9,901,753 B2 | 2/2018 | Cain et al. |
| 10,022,107 B2 | 7/2018 | Thornton et al. |
| 10,046,181 B2 | 8/2018 | Barthe et al. |
| 10,058,352 B2 | 8/2018 | Carvell et al. |
| 10,130,828 B2 | 11/2018 | Vortman et al. |
| 10,751,015 B2 | 8/2020 | Anderson et al. |
| 10,751,125 B2 | 8/2020 | Levy et al. |
| 10,791,991 B2 | 10/2020 | Burkett et al. |
| 10,799,209 B2 | 10/2020 | Lahti et al. |
| 10,806,421 B2 | 10/2020 | Keller |
| 10,820,813 B2 | 11/2020 | Alpert |
| 10,847,264 B2 | 11/2020 | Mansker et al. |
| 10,849,511 B2 | 12/2020 | Tochterman et al. |
| 10,869,603 B2 | 12/2020 | Millett et al. |
| 10,869,633 B2 | 12/2020 | Burkett |
| 10,869,648 B2 | 12/2020 | Hubbard et al. |
| 10,874,353 B2 | 12/2020 | Assif |
| 10,874,409 B2 | 12/2020 | Matsubara et al. |
| 10,878,586 B2 | 12/2020 | Brokman et al. |
| 10,888,232 B2 | 1/2021 | Anderson et al. |
| 10,893,808 B2 | 1/2021 | Dorando |
| 10,905,394 B2 | 2/2021 | Stigall et al. |
| 10,912,463 B2 | 2/2021 | Davies et al. |
| 10,925,688 B2 | 2/2021 | Millett et al. |
| 10,927,003 B2 | 2/2021 | Millett et al. |
| 10,932,678 B2 | 3/2021 | Burkett |
| 10,939,826 B2 | 3/2021 | Glynn et al. |
| 10,942,022 B2 | 3/2021 | Johansson et al. |
| 10,973,419 B2 | 4/2021 | Corl |
| 10,993,618 B2 | 5/2021 | Mansker et al. |
| 10,993,628 B2 | 5/2021 | Tochterman |
| 10,993,694 B2 | 5/2021 | Meyer et al. |
| 11,000,185 B2 | 5/2021 | Stigall et al. |
| 11,006,840 B2 | 5/2021 | Stigall |
| 11,013,491 B2 | 5/2021 | Rice et al. |
| 11,020,087 B2 | 6/2021 | Hoffman |
| 11,020,089 B2 | 6/2021 | Corl |
| 11,026,591 B2 | 6/2021 | Burkett et al. |
| 11,040,140 B2 | 6/2021 | Unser et al. |
| 2001/0039420 A1 | 11/2001 | Burbank et al. |
| 2001/0041163 A1 | 11/2001 | Sugita et al. |
| 2002/0045890 A1 | 4/2002 | Celliers et al. |
| 2002/0078964 A1 | 6/2002 | Kovac et al. |
| 2002/0099356 A1 | 7/2002 | Unger et al. |
| 2002/0145091 A1 | 10/2002 | Talish et al. |
| 2003/0092982 A1 | 5/2003 | Eppstein |
| 2003/0112922 A1 | 6/2003 | Burdette et al. |
| 2003/0149352 A1 | 8/2003 | Liang et al. |
| 2003/0157025 A1 | 8/2003 | Unger et al. |
| 2003/0169591 A1 | 9/2003 | Cochran |

(56) References Cited

U.S. PATENT DOCUMENTS

| | | |
|---|---|---|
| 2003/0181833 A1 | 9/2003 | Faragalla et al. |
| 2003/0199857 A1 | 10/2003 | Eizenhofer |
| 2003/0221561 A1 | 12/2003 | Milo |
| 2003/0236539 A1 | 12/2003 | Rabiner et al. |
| 2004/0127815 A1 | 7/2004 | Marchitto et al. |
| 2004/0138563 A1 | 7/2004 | Moehring et al. |
| 2004/0162571 A1 | 8/2004 | Rabiner et al. |
| 2004/0236248 A1 | 11/2004 | Svedman |
| 2004/0243021 A1 | 12/2004 | Murphy et al. |
| 2004/0260214 A1 | 12/2004 | Echt et al. |
| 2005/0020945 A1 | 1/2005 | Tosaya et al. |
| 2005/0038339 A1 | 2/2005 | Chauhan et al. |
| 2005/0038361 A1 | 2/2005 | Zhong et al. |
| 2005/0152561 A1 | 7/2005 | Spencer |
| 2005/0154314 A1 | 7/2005 | Quistgaard |
| 2005/0154431 A1 | 7/2005 | Quistgaard et al. |
| 2005/0234438 A1 | 10/2005 | Mast et al. |
| 2005/0283098 A1 | 12/2005 | Conston et al. |
| 2006/0060991 A1 | 3/2006 | Holsteyns et al. |
| 2006/0074303 A1 | 4/2006 | Chornenky et al. |
| 2006/0173387 A1 | 8/2006 | Hansmann et al. |
| 2006/0206028 A1 | 9/2006 | Lee et al. |
| 2006/0241466 A1 | 10/2006 | Ottoboni et al. |
| 2006/0241523 A1 | 10/2006 | Sinelnikov et al. |
| 2006/0241533 A1 | 10/2006 | Geller |
| 2006/0264760 A1 | 11/2006 | Liu et al. |
| 2006/0293630 A1 | 12/2006 | Manna et al. |
| 2007/0010805 A1 | 1/2007 | Fedewa et al. |
| 2007/0016039 A1 | 1/2007 | Vortman et al. |
| 2007/0044562 A1 | 3/2007 | Sarr |
| 2007/0065420 A1 | 3/2007 | Johnson |
| 2007/0083120 A1 | 4/2007 | Cain et al. |
| 2007/0161902 A1 | 7/2007 | Dan |
| 2007/0167764 A1 | 7/2007 | Hynynen |
| 2007/0205785 A1 | 9/2007 | Nilsson |
| 2007/0219448 A1 | 9/2007 | Seip et al. |
| 2008/0013593 A1 | 1/2008 | Kawabata |
| 2008/0033297 A1 | 2/2008 | Sliwa |
| 2008/0033417 A1 | 2/2008 | Nields et al. |
| 2008/0055003 A1 | 3/2008 | Unnikrishnan et al. |
| 2008/0082026 A1 | 4/2008 | Schmidt et al. |
| 2008/0091125 A1 | 4/2008 | Owen et al. |
| 2008/0126665 A1 | 5/2008 | Burr et al. |
| 2008/0177180 A1 | 7/2008 | Azhari et al. |
| 2008/0194965 A1 | 8/2008 | Sliwa et al. |
| 2008/0214964 A1 | 9/2008 | Chapelon et al. |
| 2008/0262345 A1 | 10/2008 | Fichtinger et al. |
| 2008/0262486 A1 | 10/2008 | Zvuloni et al. |
| 2008/0312561 A1 | 12/2008 | Chauhan |
| 2008/0319376 A1 | 12/2008 | Wilcox et al. |
| 2009/0030339 A1 | 1/2009 | Cheng et al. |
| 2009/0036773 A1 | 2/2009 | Lau et al. |
| 2009/0112098 A1 | 4/2009 | Vaezy et al. |
| 2009/0177085 A1 | 7/2009 | Maxwell et al. |
| 2009/0198094 A1 | 8/2009 | Fenster et al. |
| 2009/0211587 A1 | 8/2009 | Lawrentschuk |
| 2009/0227874 A1 | 9/2009 | Suri et al. |
| 2009/0230822 A1 | 9/2009 | Kushculey et al. |
| 2009/0287083 A1 | 11/2009 | Kushculey et al. |
| 2010/0011845 A1 | 1/2010 | Laugharn et al. |
| 2010/0056924 A1 | 3/2010 | Powers |
| 2010/0059264 A1 | 3/2010 | Hasegawa et al. |
| 2010/0069797 A1 | 3/2010 | Cain et al. |
| 2010/0125225 A1 | 5/2010 | Gelbart et al. |
| 2010/0152624 A1 | 6/2010 | Tanis et al. |
| 2010/0163694 A1 | 7/2010 | Fadler et al. |
| 2010/0261994 A1 | 10/2010 | Davalos et al. |
| 2010/0274136 A1 | 10/2010 | Cerofolini |
| 2010/0286519 A1 | 11/2010 | Lee et al. |
| 2010/0298744 A1 | 11/2010 | Altshuler et al. |
| 2010/0305432 A1 | 12/2010 | Duhay et al. |
| 2010/0317971 A1 | 12/2010 | Fan et al. |
| 2010/0318002 A1 | 12/2010 | Prus et al. |
| 2011/0054315 A1 | 3/2011 | Roberts et al. |
| 2011/0112400 A1 | 5/2011 | Emery et al. |
| 2011/0118602 A1 | 5/2011 | Weng et al. |
| 2011/0144490 A1 | 6/2011 | Davis et al. |
| 2011/0144545 A1 | 6/2011 | Fan et al. |
| 2011/0172529 A1 | 7/2011 | Gertner |
| 2011/0178444 A1 | 7/2011 | Slayton et al. |
| 2011/0245671 A1* | 10/2011 | Sato .............. A61B 8/0808 600/443 |
| 2011/0251528 A1 | 10/2011 | Canney et al. |
| 2011/0257524 A1 | 10/2011 | Gertner |
| 2011/0263967 A1 | 10/2011 | Bailey et al. |
| 2011/0270136 A1* | 11/2011 | Vitek ................ A61N 7/02 601/2 |
| 2011/0319927 A1 | 12/2011 | Nita |
| 2012/0029353 A1 | 2/2012 | Slayton et al. |
| 2012/0029393 A1 | 2/2012 | Lee |
| 2012/0059264 A1 | 3/2012 | Hope Simpson et al. |
| 2012/0059285 A1 | 3/2012 | Soltani et al. |
| 2012/0092724 A1 | 4/2012 | Pettis |
| 2012/0130288 A1 | 5/2012 | Holland et al. |
| 2012/0136279 A1 | 5/2012 | Tanaka et al. |
| 2012/0158013 A1 | 6/2012 | Stefanchik et al. |
| 2012/0172720 A1 | 7/2012 | Asami et al. |
| 2012/0189998 A1 | 7/2012 | Kruecker et al. |
| 2012/0215157 A1 | 8/2012 | Berryman et al. |
| 2012/0232388 A1 | 9/2012 | Curra et al. |
| 2012/0259250 A1 | 10/2012 | Sapozhnikov et al. |
| 2012/0271167 A1 | 10/2012 | Holland et al. |
| 2012/0271223 A1 | 10/2012 | Khanna |
| 2013/0051178 A1 | 2/2013 | Rybyanets |
| 2013/0053691 A1 | 2/2013 | Kawabata et al. |
| 2013/0090579 A1 | 4/2013 | Cain et al. |
| 2013/0102932 A1 | 4/2013 | Cain et al. |
| 2013/0144165 A1 | 6/2013 | Ebbini et al. |
| 2013/0190623 A1 | 7/2013 | Bertolina et al. |
| 2013/0255426 A1 | 10/2013 | Kassow et al. |
| 2013/0303906 A1 | 11/2013 | Cain et al. |
| 2014/0058293 A1 | 2/2014 | Hynynen et al. |
| 2014/0073995 A1 | 3/2014 | Teofilovic et al. |
| 2014/0074076 A1 | 3/2014 | Gertner |
| 2014/0088613 A1 | 3/2014 | Seo et al. |
| 2014/0100459 A1 | 4/2014 | Xu et al. |
| 2014/0128734 A1 | 5/2014 | Genstler et al. |
| 2014/0200489 A1 | 7/2014 | Behar et al. |
| 2014/0330124 A1 | 11/2014 | Carol |
| 2014/0378832 A1 | 12/2014 | Sanghvi et al. |
| 2015/0011916 A1 | 1/2015 | Cannata et al. |
| 2015/0063668 A1 | 3/2015 | You et al. |
| 2015/0151141 A1 | 6/2015 | Arnal et al. |
| 2015/0190121 A1 | 7/2015 | Slayton et al. |
| 2015/0258352 A1 | 9/2015 | Lin et al. |
| 2015/0273246 A1 | 10/2015 | Darlington et al. |
| 2015/0297177 A1 | 10/2015 | Boctor et al. |
| 2015/0375015 A1 | 12/2015 | Cain |
| 2016/0114194 A1 | 4/2016 | Gertner |
| 2016/0135916 A1 | 5/2016 | Rakic et al. |
| 2016/0151618 A1 | 6/2016 | Powers et al. |
| 2016/0184614 A1 | 6/2016 | Matula et al. |
| 2016/0184616 A1 | 6/2016 | Cain et al. |
| 2016/0206341 A1 | 7/2016 | Slayton |
| 2016/0206867 A1 | 7/2016 | Hossack et al. |
| 2016/0287909 A1 | 10/2016 | Maxwell et al. |
| 2016/0303166 A1 | 10/2016 | Katz et al. |
| 2016/0339273 A1 | 11/2016 | Al Mayiah |
| 2016/0354087 A1 | 12/2016 | Noonan et al. |
| 2017/0000376 A1 | 1/2017 | Partanen et al. |
| 2017/0049463 A1 | 2/2017 | Popovic et al. |
| 2017/0071515 A1 | 3/2017 | Chevillet et al. |
| 2017/0072227 A1 | 3/2017 | Khokhlova et al. |
| 2017/0072228 A1 | 3/2017 | Wang et al. |
| 2017/0100145 A1 | 4/2017 | Khoklova et al. |
| 2017/0120080 A1 | 5/2017 | Phillips et al. |
| 2017/0165046 A1* | 6/2017 | Johnson .............. A61L 31/18 |
| 2018/0064412 A1 | 3/2018 | Messas et al. |
| 2018/0317884 A1 | 11/2018 | Chapelon et al. |
| 2019/0216478 A1 | 7/2019 | Maxwell et al. |
| 2019/0275353 A1 | 9/2019 | Cannata et al. |
| 2020/0164231 A1 | 5/2020 | Cannata et al. |
| 2020/0253550 A1 | 8/2020 | Nair |
| 2020/0260964 A1 | 8/2020 | Collins et al. |

(56) References Cited

U.S. PATENT DOCUMENTS

| | | |
|---|---|---|
| 2020/0330039 A1 | 10/2020 | Burkett et al. |
| 2020/0330075 A1 | 10/2020 | O'Reilly et al. |
| 2020/0346046 A1 | 11/2020 | Cannata et al. |
| 2020/0367835 A1 | 11/2020 | Anderson |
| 2020/0405259 A1 | 12/2020 | Merritt |
| 2021/0000541 A1 | 1/2021 | Levy et al. |
| 2021/0008394 A1 | 1/2021 | Cain et al. |
| 2021/0022703 A1 | 1/2021 | Nair |
| 2021/0161398 A1 | 6/2021 | Millett et al. |

FOREIGN PATENT DOCUMENTS

| | | |
|---|---|---|
| CN | 201197744 Y | 2/2009 |
| CN | 102292123 A | 12/2011 |
| CN | 102481164 A | 5/2012 |
| CN | 102665585 A | 9/2012 |
| CN | 103537016 A | 1/2014 |
| CN | 103648361 A | 3/2014 |
| CN | 103812477 A | 5/2014 |
| CN | 104013444 A | 9/2014 |
| CN | 104135938 A | 11/2014 |
| CN | 106999053 B | 10/2020 |
| CN | 107660137 B | 10/2020 |
| CN | 106661535 B | 3/2021 |
| CN | 106999054 B | 5/2021 |
| CN | 106793997 B | 6/2021 |
| CN | 107530049 B | 6/2021 |
| DE | 3220751 A1 | 12/1983 |
| DE | 3544628 A1 | 6/1987 |
| DE | 3817094 A1 | 11/1989 |
| DE | 4012760 A1 | 5/1992 |
| EP | 0017382 A1 | 10/1980 |
| EP | 0320303 A2 | 6/1989 |
| EP | 0332871 A2 | 9/1989 |
| EP | 0384831 A2 | 8/1990 |
| EP | 0755653 A1 | 1/1997 |
| EP | 1374785 A1 | 1/2004 |
| EP | 1504713 A1 | 2/2005 |
| EP | 2397188 A1 | 12/2011 |
| EP | 2759003 B1 | 8/2020 |
| EP | 3218629 B1 | 10/2020 |
| EP | 3229688 B1 | 10/2020 |
| EP | 2887989 B1 | 2/2021 |
| EP | 3777689 A1 | 2/2021 |
| EP | 2938253 B1 | 3/2021 |
| EP | 3076864 B1 | 3/2021 |
| EP | 2802276 B1 | 4/2021 |
| EP | 2809221 B1 | 4/2021 |
| EP | 2967369 B1 | 5/2021 |
| EP | 2967488 B1 | 6/2021 |
| EP | 3184048 B1 | 6/2021 |
| ES | 2819552 T3 | 4/2021 |
| GB | 2099582 A | 12/1982 |
| IL | 254768 A | 5/2021 |
| JP | 60-80779 A | 5/1985 |
| JP | 61-196718 A | 8/1986 |
| JP | 02-215451 A | 8/1990 |
| JP | H0422351 A | 1/1992 |
| JP | 06-197907 A | 7/1994 |
| JP | 07-504339 A | 5/1995 |
| JP | 08-84740 A | 4/1996 |
| JP | 06-304178 A | 5/1996 |
| JP | 08-131454 A | 5/1996 |
| JP | 09-55571 A | 2/1997 |
| JP | 10-512477 A | 12/1998 |
| JP | 2000300559 A | 10/2000 |
| JP | 2003510159 A | 3/2003 |
| JP | 2004505660 A | 2/2004 |
| JP | 2004249106 A | 9/2004 |
| JP | 2005167058 A | 6/2005 |
| JP | 2006511265 A | 4/2006 |
| JP | 2007144225 A | 6/2007 |
| JP | 2007520307 A | 7/2007 |
| JP | 2010019554 A | 1/2010 |
| JP | 2010029650 A | 2/2010 |
| JP | 2010204068 A | 9/2010 |
| JP | 2013538097 A | 10/2013 |
| JP | 2004512502 A | 4/2014 |
| JP | 2015519970 A | 7/2015 |
| JP | 2016508808 A | 3/2016 |
| JP | 06785554 B2 | 10/2020 |
| JP | 06789944 B2 | 11/2020 |
| JP | 2020195788 A | 12/2020 |
| JP | 6832958 B2 | 2/2021 |
| JP | 6835719 B2 | 2/2021 |
| JP | 6838057 B2 | 3/2021 |
| JP | 6849592 B2 | 3/2021 |
| JP | 6896719 B2 | 6/2021 |
| WO | WO94/06355 A1 | 3/1994 |
| WO | WO02/32506 A1 | 4/2002 |
| WO | WO2005/018469 A1 | 3/2005 |
| WO | WO2008/051484 A2 | 5/2008 |
| WO | WO2011/040054 A1 | 7/2011 |
| WO | WO2011/092683 A1 | 8/2011 |
| WO | WO2011/154654 A2 | 12/2011 |
| WO | WO2014/008594 A1 | 1/2014 |
| WO | WO2014/071386 A1 | 5/2014 |
| WO | WO2015/000953 A1 | 1/2015 |

OTHER PUBLICATIONS

Shung; Diagnostic Ultrasound: Imaging and Blood Flow Measurements; Taylor and Francis Group, LLC; Boca Raton, FL; 207 pages; (year of pub. sufficiently earlier than effective US filing date and any foreign priority date) 2006.

Akiyama et al.; Elliptically curved acoustic lens for emitting strongly focused finite-amplitude beams: Application of the spheroidal beam equation model to the theoretical prediction; Acoustical Science and Technology, vol. 26, pp. 279-284, May 2005.

Appel et al.; Stereoscopic highspeed recording of bubble filaments; Ultrasonics Sonochemistry; vol. 11(1); pp. 39-42; Jan. 2004.

Arani et al.; Transurethral prostate magnetic resonance elestography; prospective imaging requirements; Magn. Reson. Med.; 65(2); pp. 340-349; Feb. 2011.

Aschoff et al.; How does alteration of hepatic blood flow affect liver perfusion and radiofrequency-induced thermal lesion size in rabbit liver?; J Magn Reson Imaging; 13(1); pp. 57-63; Jan. 2001.

Atchley et al.; Thresholds for cavitation produced in water by pulsed ultrasound; Ultrasonics.; vol. 26(5); pp. 280-285; Sep. 1988.

Avago Technologies; ACNV2601 High Insulation Voltage 10 MBd Digital Opotcoupler. Avago Technologies Data Sheet; pp. 1-11; Jul. 29, 2010.

Avago Technologies; Avago's ACNV2601 optocoupler is an optically coupled logic gate; Data Sheet; 2 pages; Jul. 29, 2010.

Avtech; AVR-8 Data sheet; May 23, 2004; 3 pages; retrieved from the internet (http//www.avtechpulse.com).

Billson et al.; Rapid prototyping technologies for ultrasonic beam focussing in NDE; IEEE International Ultrasonic Symposium Proceedings; pp. 2472-2474; Oct. 2011.

Bjoerk et al.; Cool/MOS CP—How to make most beneficial use of the generation of super junction technology devices. Infineon Technologies AG. [retrieved Feb. 4, 2014] from the internet (http://www.infineon.com/dgdl/Infineon+-+Application+Note+-+PowerMOSFETs+-+600V+CoolMOS%E284%A2+-+CP+Most+beneficial+use+of+superjunction+technologie+devices.pdf? folderId=db3a304412b407950112b408e8c90004&fileId=db3a304412b407950112b40ac9a40688>pages1,4.14; Feb. 2007.

Bland et al.; Surgical Oncology; McGraw Hill; Chap. 5 (Cavitron Ultrasonic Aspirator); pp. 461-462; Jan. 29, 2001.

Burdin et al.; Implementation of the laser diffraction technique for cavitation bubble investigations; Particle & Particle Systems Characterization; vol. 19; pp. 73-83; May 2002.

Cain, Charles A.; Histotripsy: controlled mechanical sub-division of soft tissues by high intensity pulsed ultrasound (conference presentation); American Institute of Physics (AIP) Therapeutic Ultrasound: 5th International Symposium on Therapeutic Ultrasound; 44 pgs.; Oct. 27-29, 2005.

(56) References Cited

OTHER PUBLICATIONS

Canney et al.; Shock-Induced Heating and Millisecond Boiling in Gels and Tissue Due to High Intensity Focused Ultrasound; Ultrasound in Medicine & Biology, vol. 36, pp. 250-267; Feb. 2010 (author manuscript).
Chan et al.; An image-guided high intensity focused ultrasound device for uterine fibroids treatment; Medical Physics, vol. 29, pp. 2611-2620, Nov. 2002.
Clasen et al.; MR-guided radiofrequency ablation of hepatocellular carcinoma: Long-term effectiveness; J Vasc Interv Radiol; 22(6); pp. 762-770; Jun. 2011.
Clement et al.; A hemisphere array for non-invasive ultrasound brain therapy and surgery; Physics in Medicine and Biology, vol. 45, p. 3707-3719, Dec. 2000.
Cline et al.; Magnetic resonance-guided thermal surgery; Magnetic Resonance in Medicine; 30(1); pp. 98-106; Jul. 1993.
Curiel et al.; Elastography for the follow-up of high-intensity focused ultrasound prostate cancer treatment: Initial comparison with MRI; Ultrasound Med. Biol; 31(11); pp. 1461-1468; Nov. 2005.
Desilets et al.; The Design of Efficient Broad-Band Piezoelectric Transducers; Sonics and Ultrasonics, IEEE Transactions on, vol. 25, pp. 115-125, May 1978.
Emelianov et al.; Triplex ultrasound: Elasticity imaging to age deep venous thrombosis; Ultrasound Med Biol; 28(6); pp. 757-767; Jun. 2002.
Giannatsis et al.; Additive fabrication technologies applied to medicine and health care: a review; The International Journal of Advanced Manufacturing Technology; 40(1-2); pp. 116-127; Jan. 2009.
Gudra et al.; Influence of acoustic impedance of multilayer acoustic systems on the transfer function of ultrasonic airborne transducers; Ultrasonics, vol. 40, pp. 457-463, May 2002.
Hall et al.; A Low Cost Compact 512 Channel Therapeutic Ultrasound System for Transcutaneous Ultrasound Surgery; AIP Conference Proceedings, Boston, MA; vol. 829, pp. 445-449, Oct. 27-29, 2005.
Hall et al.; Acoustic Access to the Prostate for Extracorporeal Ultrasound Ablation; Journal of Endourology, vol. 24, pp. 1875-1881, Nov. 2010.
Hall et al.; Histotripsy of the prostate: dose effects in a chronic canine model; Urology; 74(4); pp. 932-937; Oct. 2009 (author manuscript).
Hall et al.; Imaging feedback of tissue liquefaction (histotripsy) in ultrasound surgery; IEEE Ultrasonic Symposium, Sep. 18-21, 2005, pp. 1732-1734.
Hartmann; Ultrasonic properties of poly(4-methyl pentene-1), Journal of Applied Physics, vol. 51, pp. 310-314, Jan. 1980.
Hobarth et al.; Color flow doppler sonography for extracorporal shock wave lithotripsy; Journal of Urology; 150(6); pp. 1768-1770; Dec. 1, 1993.
Holland et al.; Thresholds for transient cavitation produced by pulsed ultrasound in a controlled nuclei environment; J. Acoust. Soc. Am.; vol. 88(5); pp. 2059-2069; Nov. 1990.
Huber et al.; Influence of shock wave pressure amplitude and pulse repetition frequency on the lifespan, size and number of transient cavities in the field of an electromagnetic lithotripter; Physics in Medicine and Biology; vol. 43(10); pp. 3113-3128; Oct. 1998.
Hynynen et al.; Tissue thermometry during ultrasound exposure; European Urology; 23(Suppl 1); pp. 12-16; (year of pub. sufficiently earlier than effective US filing date and any foreign priority date)1993.
Kallel et al.; The feasibility of elastographic visualization of HIFU-induced thermal lesions in soft tissues: Image-guided high-intensity focused ultrasound; Ultrasound Med. Biol; 25(4); pp. 641-647; May 1999.
Khokhlova et al.; Controlled tissue emulsification produced by high intensity focused ultrasound shock waves and millisecond boiling; J. Acoust. Soc. Am.; 130(5), pt. 2; pp. 3498-3510; Nov. 2011.
Kim et al.; Dependence of particle volume fraction on sound velocity and attenuation of EPDM composites; Ultrasonics, vol. 46, pp. 177-183, Feb. 2007.
Konofagou; Quo vadis elasticity imaging?; Ultrasonics; 42(1-9); pp. 331-336; Apr. 2004.
Krimholtz et al.; New equivalent circuits for elementary piezoelectric transducers; Electronics Letters, vol. 6, pp. 398-399, Jun. 1970.
Kruse et al.; Tissue characterization using magnetic resonance elastography: Preliminary results; Phys. Med. Biol; 45(6); pp. 1579-1590; Jun. 2000.
Lake et al.; Histotripsy: minimally invasive technology for prostatic tissue ablation in an in vivo canine model; Urology; 72(3); pp. 682-686; Sep. 2008.
Lauterborn et al.; Cavitation bubble dynamics studied by high speed photography and holography: part one; Ultrasonics; vol. 23; pp. 260-268; Nov. 1985.
Lensing et al.; Deep-vein thrombosis; The Lancet, vol. 353, pp. 479-485, Feb. 6, 1999.
Lin et al; Dual-beam histotripsy: a low-frequency pump enabling a high-frequency probe for precise lesion formation; IEEE Trans. Ultrason. Ferroelectr. Control; 61(2); pp. 325-340; Feb. 2014; (Author Manuscript; 29 pages).
Liu et al.; Real-time 2-D temperature imaging using ultrasound; IEEE Trans Biomed Eng; 57(1); pp. 12-16; Jan. 2010 (author manuscript, 16 pgs.).
Liu et al.; Viscoelastic property measurement in thin tissue constructs using ultrasound; IEEE Trans Ultrason Ferroelectr Freq Control; 55(2); pp. 368-383; Feb. 2008 (author manuscript, 37 pgs.).
Manes et al.; Design of a Simplified Delay System for Ultrasound Phased Array Imaging; Sonics and Ultrasonics, IEEE Transactions on, vol. 30, pp. 350-354, Nov. 1983.
Maréchal et al; Effect of Radial Displacement of Lens on Response of Focused Ultrasonic Transducer; Japanese Journal of Applied Physics, vol. 46, p. 3077-3085; May 15, 2007.
Maréchal et al; Lens-focused transducer modeling using an extended KLM model; Ultrasonics, vol. 46, pp. 155-167, May 2007.
Martin et al.; Water-cooled, high-intensity ultrasound surgical applicators with frequency tracking; Ultrasonics, Ferroelectrics and Frequency Control, IEEE Transactions on, vol. 50, pp. 1305-1317, Oct. 2003.
Maxwell et al.; Cavitation clouds created by shock scattering from bubbles during histotripsy; J. Acoust. Soc. Am.; 130(4); pp. 1888-1898; Oct. 2011.
Maxwell et al.; Noninvasive Thrombolysis Using Pulsed Ultrasound Cavitation Therapy—Histotripsy; Ultrasound in Medicine & Biology, vol. 35, pp. 1982-1994, Dec. 2009 (author manuscript).
Maxwell; Noninvasive thrombolysis using histotripsy pulsed ultrasound cavitation therapy; PhD Dissertation. University of Michigan, Ann Arbor, Michigan. Jun. 2012.
Maxwell et al.; In-vivo study of non-invasive thrombolysis by histotripsy in a porcine model; IEEE international Ultrasonics Symposium; IEEE; pp. 220-223; Sep. 20, 2009.
Miller et al.; A review of in vitro bioeffects of inertial ultrasonic cavitation from a mechanistic perspective; Ultrasound in Medicine and Biology; vol. 22; pp. 1131-1154; (year of publication is sufficiently earlier than the effective U.S. filing date and any foreign priority date) 1996.
Miller et al.; Investigation of the mechanism of ARFI-based color doppler feedback of histotripsy tissue fractionation; Ultrasonic Symposium (IUS); 2013 IEEE International; 4 pages; Jul. 21-25, 2013.
Miller et al.; Real-time elastography-based monitoring of histotripsy tissue fractionation using color doppler; Ultrasonics Symposium (IUS); 2012 IEEE International; 8 pages; Oct. 7-10, 2012.
Nightingale et al.; Analysis of contrast in images generated with transient acoustic radiation force; Ultrasound Med Biol; 32(1); pp. 61-72; Jan. 2006.
Ohl et al.; Bubble dynamics, shock waves and sonoluminescence; Phil. Trans. R. Soc. Lond. A; vol. 357; pp. 269-294; (year of publication is sufficiently earlier than the effective U.S. filing date and any foreign priority date) 1999.
Okada et al.; A case of hepatocellular carcinoma treated by MR-guided focused ultrasound ablation with respiratory gating; Magn Reson Med Sci; 5(3); pp. 167-171; Oct. 2006.
Palmeri et al.; Acoustic radiation force-based elasticity imaging methods; Interface Focus; 1; pp. 553-564; Aug. 2011.

(56) References Cited

OTHER PUBLICATIONS

Parsons et al.; Cost-effective assembly of a basic fiber-optic hydrophone for measurement of high-amplitude therapeutic ultrasound fields; The Journal of the Acoustical Society of America, vol. 119, pp. 1432-1440, Mar. 2006.
Parsons et al.; Pulsed cavitational ultrasound therapy for controlled tissue homogenization; Ultrasound in Med. & Biol.; vol. 32(1); pp. 115-129; Jan. 2006.
Pishchalnikov et al.; Cavitation Bubble Cluster Activity in the Breakage of Kidney Stones by Lithotripter Shock Waves; J Endourol.; 17(7): 435-446; Sep. 2003.
Porter et al.; Reduction in left ventricular cavitary attenuation and improvement in posterior myocardial contrast . . . ; J Am Soc Echocardiography; pp. 437-441; Jul.-Aug. 1996.
Roberts et al.; Pulsed cavitational ultrasound: a noninvasive technology for controlled tissue ablation (histotripsy) in the rabbit kidney; Journal of Urology; vol. 175(2); pp. 734-738; Feb. 2006.
Rosenschein et al.; Ultrasound Imaging-Guided Noninvasive Ultrasound Thrombolysis: Preclinical Results; Circulation; vol. 102; pp. 238-245, Jul. 11, 2000.
Rowland et al.; MRI study of hepatic tumours following high intensity focused ultrasound surgery; British Journal of Radiology; 70; pp. 144-153; Feb. 1997.
Roy et al.; A precise technique for the measurement of acoustic cavitation thresholds and some preliminary results; Journal of the Acoustical Society of America; vol. 78(5); pp. 1799-805; Nov. 1985.
Sapareto et al.; Thermal dose determination in cancer therapy; Int J Radiat Oncol Biol Phys; 10(6); pp. 787-800; Apr. 1984.
Sapozhnikov et al.; Ultrasound-Guided Localized Detection of Cavitation During Lithotripsy in Pig Kidney in Vivo; IEEE Ultrasonics Symposium, vol. 2; pp. 1347-1350; Oct. 7-10, 2001.
Sato et al.; Experimental Investigation of Phased Array Using Tapered Matching Layers. 2002 IEEE Ultrasound Symposium. vol. 2; pp. 1235-1238, Oct. 2002.
Simonin et al.; Characterization of heterogeneous structure in a polymer object manufactured by stereolithography with low-frequency microechography; Journal of Materials Chemistry; vol. 6, pp. 1595-99, Sep. 1996.
Sokolov et al.; Use of a dual-pulse lithotripter to generate a localized and intensified cavitation field; Journal of the Acoustical Society of America; vol. 110(3); pp. 1685-1695; Sep. 2001.
Song et al.; Feasibility of Using Lateral Mode Coupling Method for a Large Scale Ultrasound Phased Array for Noninvasive Transcranial Therapy; Biomedical Engineering; IEEE Transactions on, vol. 57, pp. 124-133; Jan. 2010 (author manuscript).
Souchon et al.; Visualisation of HIFU lesions using elastography of the human prostate in vivo: Preliminary results; Ultrasound Med. Biol; 29(7); pp. 1007-1015; Jul. 2003.
Souquet et al.; Design of Low-Loss Wide-Band Ultrasonic Transducers for Noninvasive Medical Application; Sonics and Ultrasonics, IEEE Transactions on, vol. 26, pp. 75-80, Mar. 1979.
Therapeutic Ultrasound Group. Non-invasive Ultrasonic Tissue Fraction for Treatment of Benign Disease and Cancer—"Histotripsy". University research [online]. Biomedical Engineering Department, University of Michigan. Jul. 2011[retrieved on Jan. 28, 2014] from: (http://web.archive.org/web/20110720091822/http://www.histotripsy.umich.edu/index.html>.entiredocument) Jul. 2011.
Toda; Narrowband impedance matching layer for high efficiency thickness mode ultrasonic transducers; Ultrasonics, Ferroelectrics and Frequency Control, IEEE Transactions on, vol. 49, pp. 299-306, Mar. 2002.

Urban et al.; Measurement of prostate viscoelasticity using shearwave dispersion ultrasound vibrometry (SDUV): an in vitro study; IEEE International Ultrasonics Symposium Proceedings (IUS); pp. 1141-1144; Oct. 11, 2010.
Van Kervel et al.; A calculation scheme for the optimum design of ultrasonic transducers; Ultrasonics, vol. 21, pp. 134-140, May 1983.
Wang et al.; Quantitative ultrasound backscatter for pulsed cavitational ultrasound therapy-histotripsy; Ultrasonics, Ferroelectrics and Frequency Control, IEEE Transactions on, vol. 56, pp. 995-1005, May 2009.
Wikipedia; Medical ultrasound; 15 pages; retrieved from the internet (https://en.wikipedia.org/w/index.php?title=Medical_utrasound&oldid=515340960) on Jan. 12, 2018.
Xie et al.; Correspondence of ultrasound elasticity imaging to direct mechanical measurement in aging DVT in rats; Ultrasound Med Biol; 31(10); pp. 1351-1359; Oct. 2005 (author manuscript, 20 pgs.).
Xu et al.; A new strategy to enhance cavitational tissue erosion by using a high intensity initiating sequence; IEEE Trans Ultrasonics Ferroelectrics and Freq Control; vol. 53(8); pp. 1412-1424; Aug. 2006.
Xu et al.; Controlled ultrasound tissue erosion: the role of dynamic interaction between insonation and microbubble activity; Journal of the Acoustical Society of America; vol. 117(1); pp. 424-435; Jan. 2005.
Xu et al.; Controlled ultrasound tissue erosion; IEEE Transaction on Ultrasonics, Ferroelectrics, and Frequency Control; vol. 51 (6); pp. 726-736; Jun. 2004.
Xu et al.; Effects of acoustic parameters on bubble cloud dynamics in ultrasound tissue erosion (histotripsy); Journal of the Acoustical Society of America; vol. 122(1); pp. 229-236; Jul. 2007.
Xu et al.; High Speed Imaging of Bubble Clouds Generated in Pulsed Ultrasound Cavitational Therapy Histotripsy; IEEE Trans Ultrason Ferroelectr Freq Control; ; vol. 54; No. 10; pp. 2091R2101; Oct. 2007.
Xu et al.; Investigation of intensity threshold for ultrasound tissue erosion; Ultrasound in Med. & Biol.; vol. 31(12); pp. 1673-1682; Dec. 2005.
Xu et al.; Optical and acoustic monitoring of bubble cloud dynamics at a tissue-fluid interface in ultrasound tissue erosion; Journal of the Acoustical Society of America; vol. 121(4); pp. 2421-2430; Apr. 2007.
Yan et al.; A review of rapid prototyping technologies and systems; Computer-Aided Design, vol. 28, pp. 307-318, Apr. 1996.
Zhang et al.; A fast tissue stiffness-dependent elastography for HIFU-induced lesions inspection; Ultrasonics; 51(8); pp. 857-869; Dec. 2011.
Zheng et al.; An acoustic backscatter-based method for localization of lesions induced by high-intensity focused ultrasound; Ultrasound Med Biol; 36(4); pp. 610-622; Apr. 2010.
Hall et al.; U.S. Appl. No. 15/583,852 entitled "Method of manufacturing an ultrasound system," filed May 1, 2017.
Xu et al.; U.S. Appl. No. 15/713,441 entitled "Bubble-induced color doppler feedback during histotripsy," filed Sep. 22, 2017.
Sferrijzza et al.; Generation of high power unipolar pulse with a piezocomposite transducer; In 1999 IEEE Ultrasonics Symposium Proceedings; International Symposium (Cat. No. 99CH37027); vol. 2: pp. 1125-1128; Oct. 17, 1999.
Maxwell et al.; The role of compressional pressure in the formation of dense bubble clouds in histotripsy; 2009 IEEE International Ultrasonics Symposium; pp. 81-84; Sep. 20, 2009.
Xu et al.; U.S. Appl. No. 17/161,498 entitled Systems and methods for histotripsy immunosensitization, filed Jan. 28, 2021.

\* cited by examiner

HISTOTRIPSY THERAPY SYSTEMS AND METHODS FOR THE TREATMENT OF BRAIN TISSUE

CROSS REFERENCE TO RELATED APPLICATIONS

This application claims the benefit of U.S. Provisional Patent Application No. 62/184,179, filed Jun. 24, 2015, titled "HISTOTRIPSY THERAPY SYSTEMS AND METHODS FOR THE TREATMENT OF INTRACEREBRAL HEMORRHAGE", which is incorporated by reference in its entirety.

GOVERNMENT LICENSE RIGHTS

This invention was made with government support under grant number NS093121 awarded by the National Institute of Health. The government has certain rights in the invention.

INCORPORATION BY REFERENCE

All publications and patent applications mentioned in this specification are herein incorporated by reference to the same extent as if each individual publication or patent application was specifically and individually indicated to be incorporated by reference.

FIELD

This disclosure generally relates to treating tissue with cavitation created by ultrasound therapy. More specifically, this disclosure relates to treatment of brain tissue or disorders of the brain, such as intracerebral hemorrhage (ICH) or brain tumors, with ultrasound therapy.

BACKGROUND

Histotripsy, or pulsed ultrasound cavitation therapy, is a technology where extremely short, intense bursts of acoustic energy induce controlled cavitation (microbubble formation) within the focal volume. The vigorous expansion and collapse of these microbubbles mechanically homogenizes cells and tissue structures within the focal volume. This is a very different end result than the coagulative necrosis characteristic of thermal ablation. To operate within a non-thermal, Histotripsy realm; it is necessary to deliver acoustic energy in the form of high amplitude acoustic pulses with low duty cycle.

Compared with conventional focused ultrasound technologies, Histotripsy has important advantages: 1) the destructive process at the focus is mechanical, not thermal; 2) bubble clouds appear bright on ultrasound imaging thereby confirming correct targeting and localization of treatment; 3) treated tissue appears darker (hypoechoic) on ultrasound imaging, so that the operator knows what has been treated; and 4) Histotripsy produces lesions in a controlled and precise manner. It is important to emphasize that unlike microwave, radiofrequency, or high-intensity focused ultrasound (HIFU), Histotripsy is not a thermal modality.

The rupture of blood vessels in the brain can lead to bleeding and clotting (hematoma) inside the brain, termed as hemorrhagic stroke or intracerebral hemorrhage (ICH). ICH accounts for 10-15% of all strokes. Current mainstay treatment remains craniotomy, a highly invasive surgery to remove the clot, associated with severe damage to the brain neurological function.

Minimally invasive (MIS) stereotactic approaches have been investigated to drain the hematoma via a catheter and thrombolytic drug (tPA) over several days. However, there are severe complications associated with tPA, and the functional outcome for ICH survivors is not improved, likely due the long treatment time allowing neurological damage to develop.

Recent preclinical studies show that, using magnetic resonance guided focused ultrasound (MRgFUS) applied outside the skullcap, the clot in the brain can be liquefied without drugs and aspirated out with a needle. However, the MRgFUS treatment time is still not short enough to avoid neurological damage (up to 3 hours for 40 mL clot). It is highly costly due to the long MRI time required, and cannot treat clots within 2 cm distance from the skullcap.

A skullcap in the ultrasound pathway can cause significant attenuation and defocusing (aberration effect) of ultrasound signals passing through the skullcap. For aberration correction, MRgFUS uses a skullcap profile extracted from prior 3D CT scans of the patient brain. However, during MRgFUS treatment, as it is impossible to put the patient in the exact same position as the previous scan, MRI is needed to guide and monitor precise focusing through the skullcap. The process is complex and highly costly.

Furthermore, all the current methods are not effective for large hematoma (>40 mL). There is a clear unmet need for a better ICH therapy that can minimally invasively and rapidly reduce the hematoma in the brain without tPA, which will allow the ICH patients to recover without significant neurological damage.

SUMMARY OF THE DISCLOSURE

Histotripsy produces tissue fractionation through dense energetic bubble clouds generated by short, high-pressure, ultrasound pulses. When using pulses shorter than 2 cycles, the generation of these energetic bubble clouds only depends on where the peak negative pressure (P−) exceeds an intrinsic threshold for inducing cavitation in a medium (typically 26-30 MPa in soft tissue with high water content).

A method of transmitting ultrasound energy into a brain of a human patient is provided, comprising the steps of placing a drainage catheter within a target tissue in the brain of the human patient, positioning a focus of a plurality of transducer elements of a therapy transducer within the target tissue, transmitting ultrasound pulses from each of the plurality of transducer elements into the target tissue, detecting the ultrasound pulses with one or more piezoelectric sensors positioned on or in the drainage catheter, and adjusting the transmission of ultrasound pulses from the plurality of transducer elements with an aberration correction algorithm based on the detected ultrasound pulses to automatically correct for an aberration effect caused by the ultrasound pulses passing through a skullcap of the human patient.

In one embodiment, the target tissue comprises a clot or hemorrhage. In another embodiment, the target tissue comprises a brain tumor.

In another embodiment, the method further comprises forming a bubble cloud on the target tissue with the ultrasound pulses.

In some embodiments, the method further comprises liquefying the target tissue with the ultrasound pulses.

In another embodiment, the method comprises draining the liquefied target tissue from the brain with the drainage catheter.

In one embodiment, adjusting the transmission of ultrasound pulses from the plurality of transducer elements with the aberration correction algorithm based on the detected ultrasound pulses further comprises determining a propagation time for the ultrasound pulses to travel from each of the plurality of transducer elements of the therapy transducer to the one or more piezoelectric sensors, calculating a time delay of the propagation time between each of the plurality of transducer elements and a reference element of the therapy transducer, and adjusting the transmission of ultrasound pulses from the plurality of transducer elements based on the calculated time delays.

In one embodiment, the one or more piezoelectric sensors comprises first and second piezoelectric sensors. In this embodiment, adjusting the transmission of ultrasound pulses from the plurality of transducer elements with the aberration correction algorithm based on the detected ultrasound pulses further comprises determining a propagation time for the ultrasound pulses to travel from each of a plurality of transducer elements of the therapy transducer to the first and second piezoelectric sensors, calculating a distance between the first and second piezoelectric sensors using projections of the first and second piezoelectric sensors onto a ray from each of the plurality of transducer elements to a midpoint of the first and second piezoelectric sensors, calculating a travel direction and a time of travel of the ultrasound pulses from each of the plurality of transducer elements to the midpoint of the first and second piezoelectric sensors, calculating a stand-off distance between the focus and the midpoint for each of the plurality of transducer elements, and calculating a time delay of each of the plurality of transducer elements based on the distance between the first and second piezoelectric sensors, the midpoint, and the stand-off distance.

In one embodiment, the method comprises placing the one or more piezoelectric sensors within or adjacent to the focus. In another embodiment, the placing step further comprises advancing the drainage catheter through a hole of the therapy transducer.

In another embodiment, the method comprises electronically or mechanically steering the focus to fully liquefy the target tissue.

An ultrasound system configured to treat a target tissue in a brain of a human patient is also provided, comprising a pulse generator and an amplifier, an ultrasound therapy transducer coupled to the pulse generator and the amplifier and having a plurality of transducer elements configured to transmit ultrasound pulses through a skullcap of the human patient towards a focal point within the target tissue in the brain to generate cavitation, a drainage catheter comprising one or more piezoelectric sensors, the drainage catheter adapted to be placed within the brain near the focal point to measure the ultrasound pulses, an electronic controller coupled to the pulse generator, the amplifier, the ultrasound therapy transducer, and the piezoelectric sensors of the drainage catheter, the electronic controller being configured to control transmission of the ultrasound pulses and adjust the transmission of ultrasound pulses from each of the plurality of transducer elements by executing an aberration correction algorithm based on the ultrasound pulses detected by the drainage catheter to automatically correct for an aberration effect caused by the ultrasound pulses passing through the skullcap of the human patient.

In one embodiment, the ultrasound therapy transducer is configured to transmit histotripsy therapy pulses to generate cavitation to liquefy the target tissue within the brain of the human patient.

In another embodiment, the drainage catheter includes drainage ports configured to drain the liquefied target tissue from the human patient.

In some embodiments, the one or more piezoelectric sensors comprises exactly one piezoelectric sensor. In this embodiment, the aberration correction algorithm comprises determining a propagation time for the ultrasound pulses to travel from each of the plurality of transducer elements of the therapy transducer to piezoelectric sensor, calculating a time delay of the propagation time between each of the plurality of transducer elements and a reference element of the therapy transducer, and adjusting the transmission of ultrasound pulses from the plurality of transducer elements based on the calculated time delays.

In some embodiments, the one or more piezoelectric sensors comprises first and second piezoelectric sensors. In this embodiment the aberration correction algorithm comprises determining a propagation time for the ultrasound pulses to travel from each of the plurality of transducer elements of the therapy transducer to the first and second piezoelectric sensors, calculating a distance between the first and second piezoelectric sensors using projections of the first and second piezoelectric sensors onto a ray from each of the plurality of transducer elements to a midpoint of the first and second piezoelectric sensors, calculating a travel direction and a time of travel of the ultrasound pulses from each of the plurality of transducer elements to the midpoint of the first and second piezoelectric sensors, calculating a stand-off distance between the focus and the midpoint for each of the plurality of transducer elements, and calculating a time delay of each of the plurality of transducer elements based on the distance between the first and second piezoelectric sensors, the midpoint, and the stand-off distance.

In one embodiment, the therapy transducer comprises a hole through which the drainage catheter is configured to be advanced into the brain of the human patient.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Histotripsy is a noninvasive, cavitation-based therapy that uses very short, high-pressure ultrasound pulses to generate a dense, energetic, lesion-producing bubble cloud. This Histotripsy treatment can create controlled tissue erosion when it is targeted at a fluid-tissue interface and welldemarcated tissue fractionation when it is targeted within bulk tissue. Additionally, Histotripsy has been shown to be capable of fragmenting model kidney stones using surface erosion that is mechanistically distinct from conventional shockwave lithotripsy (SWL). Histotripsy therapy can be guided and monitored using ultrasound B-mode imaging in real-time, since 1) the cavitating bubble cloud appears as a temporally changing hyperechoic region in B-mode imaging, allowing the treatment to be precisely targeted, and 2) the echogenicity of the targeted region decreases as the degree of tissue fractionation increases, which can be used as a way of monitoring lesion production (image feedback) in real-time.

Generally in Histotripsy treatments, ultrasound pulses with 1 or more acoustic cycles are applied, and the bubble cloud formation relies on the pressure release scattering of the positive shock fronts (sometimes exceeding 100 MPa, P+) from initially initiated, sparsely distributed bubbles (or a single bubble). This has been called the "shock scattering mechanism". This mechanism depends on one (or a few sparsely distributed) bubble(s) initiated with the initial negative half cycle(s) of the pulse at the focus of the transducer. A cloud of microbubbles then forms due to the pressure release backscattering of the high peak positive shock fronts from these sparsely initiated bubbles. These back-scattered high-amplitude rarefactional waves exceed the intrinsic threshold thus producing a localized dense bubble cloud. Each of the following acoustic cycles then induces further cavitation by the backscattering from the bubble cloud surface, which grows towards the transducer. As a result, an elongated dense bubble cloud growing along the acoustic axis opposite the ultrasound propagation direction is observed with the shock scattering mechanism. This shock scattering process makes the bubble cloud generation not only dependent on the peak negative pressure, but also the number of acoustic cycles and the amplitudes of the positive shocks. Without these intense shock fronts developed by nonlinear propagation, no dense bubble clouds are generated when the peak negative half-cycles are below the intrinsic threshold.

When ultrasound pulses less than 2 cycles are applied, shock scattering can be minimized, and the generation of a dense bubble cloud depends on one or two negative half cycle(s) of the applied ultrasound pulses exceeding an "intrinsic threshold" of the medium (the "intrinsic threshold mechanism"). This threshold can be in the range of 26-30 MPa for soft tissues with high water content, such as tissues in the human body. Using this intrinsic threshold mechanism, the spatial extent of the lesion is well-defined and more predictable. With peak negative pressures (P−) not significantly higher than this threshold, sub-wavelength reproducible lesions as small as half of the −6 dB beamwidth of a transducer can be generated.

Histotripsy has the potential to overcome the drawbacks of conventional treatment of ICH to provide minimally invasive, rapid reduction of hematoma in the brain, without thrombolytic drugs and regardless the size of the hematoma. Systems and methods described herein transmit microsecond-length ultrasound pulses at high pressures to generate a dense cavitation cloud of microbubbles using pre-existing gas nuclei in the clot within the focal region. The rapid expansion and collapse of the microbubbles induces high strain and stress to adjacent cells to fractionate the cells to liquid-like acellular homogenate.

According to some embodiments, Histotripsy can be used treat brain tissue or disorders of the brain, such as ICH or brain tumors. In one embodiment, Histotripsy can be used to liquefy a clot or a brain tumor through a skullcap of a human patient, and the resulting liquid can then be drained via a drainage catheter, without the use of thrombolytic drugs or external agents. For example, Histotripsy can be used to liquefy in vitro clots of 40 mL through a human skullcap within 30 minutes, which is six-fold faster than MRgFUS. With parameter optimization, the treatment time can be shortened by more than an order of magnitude compared to MRgFUS. These optimized parameters can be used to treat clots larger than 40 mL and at locations within 2 cm to the skullcap. The systems and methods described herein enable rapid clot removal even for clots >40 mL, in a minimally invasive approach, and eliminate the need for thrombolytic drugs and MRI, thereby substantially improving ICH and brain tumor therapy.

According to embodiments described herein that use histotripsy for treating the brain, a catheter can be placed in a target tissue, such as a clot or tumor within the brain of a patient. One or more acoustic hydrophones or PZT sensors can be integrated to a guidewire placed inside the catheter, which can then be inserted into the target tissue in the brain to directly measure ultrasound signals from a histotripsy therapy transducer positioned outside the patient. The timing of pulse transmission from all elements of the histotripsy therapy transducer can be re-aligned to refocus through the skullcap by using the timing of the ultrasound signal received at the sensor from each element of histotripsy therapy transducer. The sensor(s) and associated aberration correction algorithm for transcranial histotripsy therapy described herein is novel and can provide a cost-effective and simplified device to guide and monitor transcranial histotripsy therapy without CT or MRI.

Figure 1:
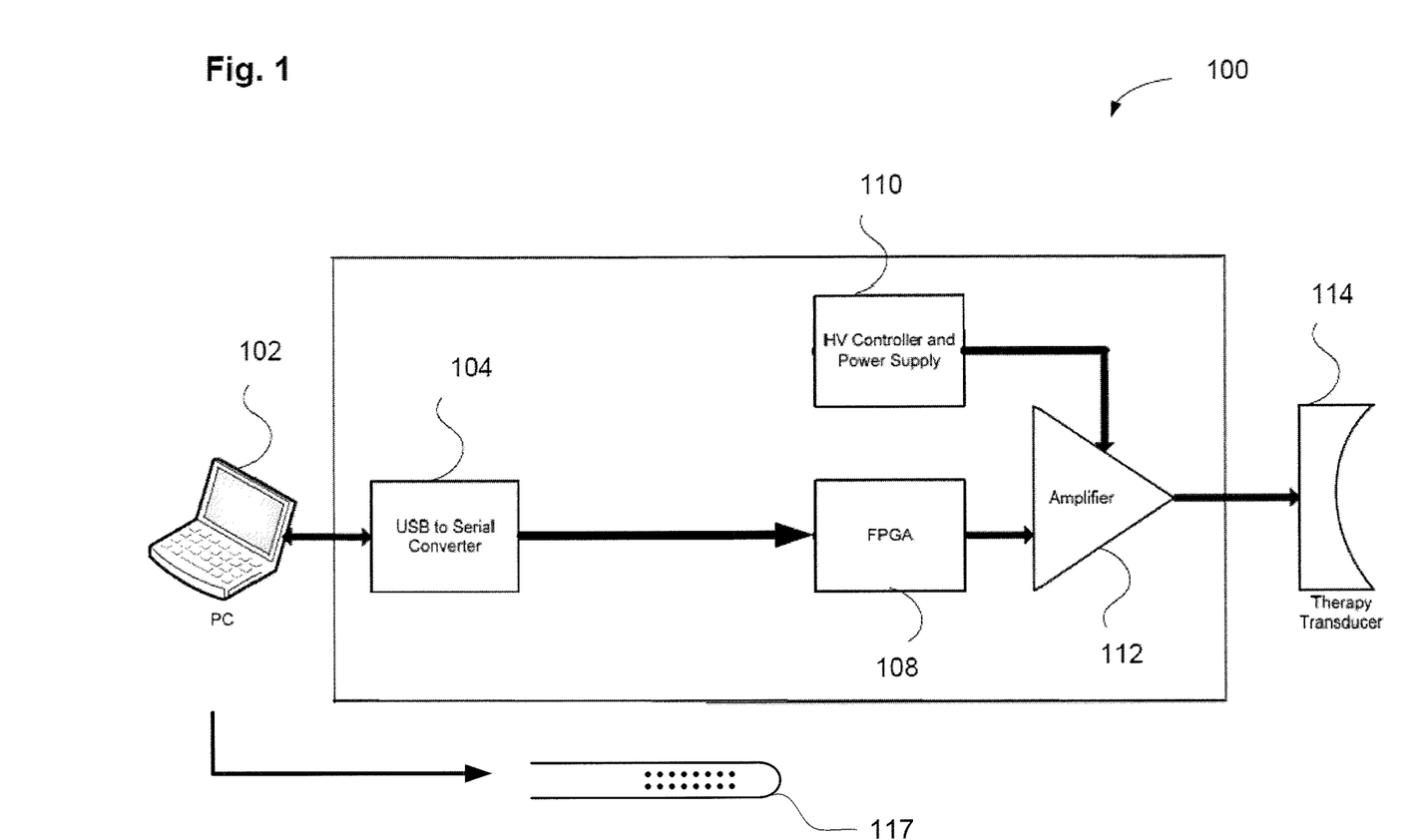
FIG. 1 shows a Histotripsy therapy system.

FIG. 1 illustrates a Histotripsy system configured to generate cavitation bubbles or bubble clouds in tissue according to the methods and embodiments described herein. A Histotripsy system and generator is configured to generate complex waveforms in order to support the ultrasound pulse sequences described herein. A simplified block diagram of system 100 is shown in FIG. 1. The main components of the system are: Computer/controller 102, USB to Serial Converter 104, FPGA (Field Programmable Gate Array) 108, High Voltage Controller and Power Supply 110, Amplifier 112, and Therapy Transducer 114, and Drainage Catheter 117.

All controls for the generator can be established using a "Histotripsy Service Tool" software that can run on the computer/controller 102 (e.g., a standard PC, laptop, tablet, or other electronic computing system) and communicates to the generator via a connector such as a wireless, USB, or serial communication 104. The controller 102 can include a non-transitory computer-readable storage medium configured to store a set of instructions capable of being executed by the controller.

The system 100 can be configured to receive multiple sets of different driving parameters and loop them, which give the ability to the user to create wide range of custom sequences where all parameters (pulse repetition frequency (PRF), voltage amplitude, number of cycles, number of pulses per set, frequency, transducer element channels enabled, and time delays) can be set differently for every pulse generated. Time delays between pulses can be specified by the PRF for a parameter set or by specifying them manually/individually on a pulse-by-pulse basis.

For overall voltage amplitude regulation, level of high voltage can be changed accordingly through the HV Controller 110. This method cannot be used for dynamic voltage amplitude changes between two pulses since it will take too long for all capacitors on the HV line to discharge. For dynamic voltage amplitude changes between pulses, PWM (pulse width modulation) can be used at the FPGA 108 where the duty cycle of the capacitor-charging pulse may be modulated in order to produce the desired pulse voltage and resultant pressure amplitude.

USB to Serial Converter

USB to Serial converter 104 can convert USB combination to serial in order to communicate from the PC or electronic controller to the FPGA. It should be understood that other converters (or none at all) may be used in embodiments where the connection between the generator and the controller is not a USB connection.

FPGA

The FPGA 108 receives the information from the PC or electronic controller 102 and it can generate the complex pulsing sequence that is required to drive the amplifier 112. The FPGA can run on 100 MHz clock since speed of pulsing is critical to be timed in at least 10 ns increments.

High Voltage Controller and Power Supply

The High Voltage Controller and Power Supply 110 determines the level of DC voltage that needs to be supplied to the amplifier circuitry in order to have an adequate voltage amplitude level at the output of the amplifier.

Amplifier

The Amplifier 112 receives pulses generated by the FPGA and is supplied with high voltage from High Voltage Controller and Power Supply. It generates high voltage amplitude pulses that are fed to the Therapy Transducer 114 through the matching network components which properly matches the impedance of the therapy transducer to the impedance of the amplifier. It can be necessary to use a large number of capacitors that can store enough energy to support peak current demand during the generation of high voltage amplitude pulses.

Therapy Transducer

The Therapy Transducer 114 can be a single element transducer, or a multi-element ultrasound therapy transducer comprising a plurality of transducer elements and configured to generate and deliver the ultrasound therapy pulses described herein into tissue or other mediums. In some embodiments, the multi-element ultrasound therapy transducer can generate ultrasound pulses in two or more frequencies. The active transducer elements of the Therapy Transducer can be piezoelectric transducer elements. In some embodiments, the transducer elements can be mounted to an acoustic lens with a common geometric focus.

In other embodiments, the transducer elements can comprise a phased array that is optimized with steering parameters to maximize treatment speed and locations for transcranial histotripsy clot liquefaction without overheating the skullcap. Overheating the skullcap is the major limitation to restrain the treatment speed and location for transcranial ultrasound therapy. Proposed parameter optimization will ensure a rapid brain tissue treatment and minimize the heating to the skullcap. In some embodiments, the therapy transducer can achieve brain tissue liquefaction rates greater than 1 mL/min, which is orders of magnitude faster than passive thrombolytic action.

The therapy transducer can be configured to generate cavitation through the skullcap with a single ultrasound pulse having one high negative pressure phase lasting approximately 1-4 is, where the peak negative pressure of the pulse directly exceeds the "intrinsic threshold" for cavitation of the medium (approximately 27 MPa for brain tissue such as clots). The focus of the therapy transducer can be electrically steered to other locations to cover a large treatment volume, and the treatment time can be shortened by more than an order of magnitude compared to other therapy modalities. In some embodiments, the focal steering rate can be kept below 1% duty cycle to avoid overheating the skullcap.

According to the systems and methods described herein, histotripsy brain therapy can be performed without real-time imaging. CT scan may be needed as part of the target tissue diagnosis but is performed prior to the treatment. Using prior CT scan and stereotactic approach, the drainage hydrophone can be placed inside the clot, and the precise position of the catheter tip with regard to the clot position is known. The focus from the histotripsy therapy transducer can then be steered to liquefy a large portion of the brain tissue, leaving a thin rim of the tissue to avoid damage to adjacent brain tissue.

Drainage Catheter

Figure 2:
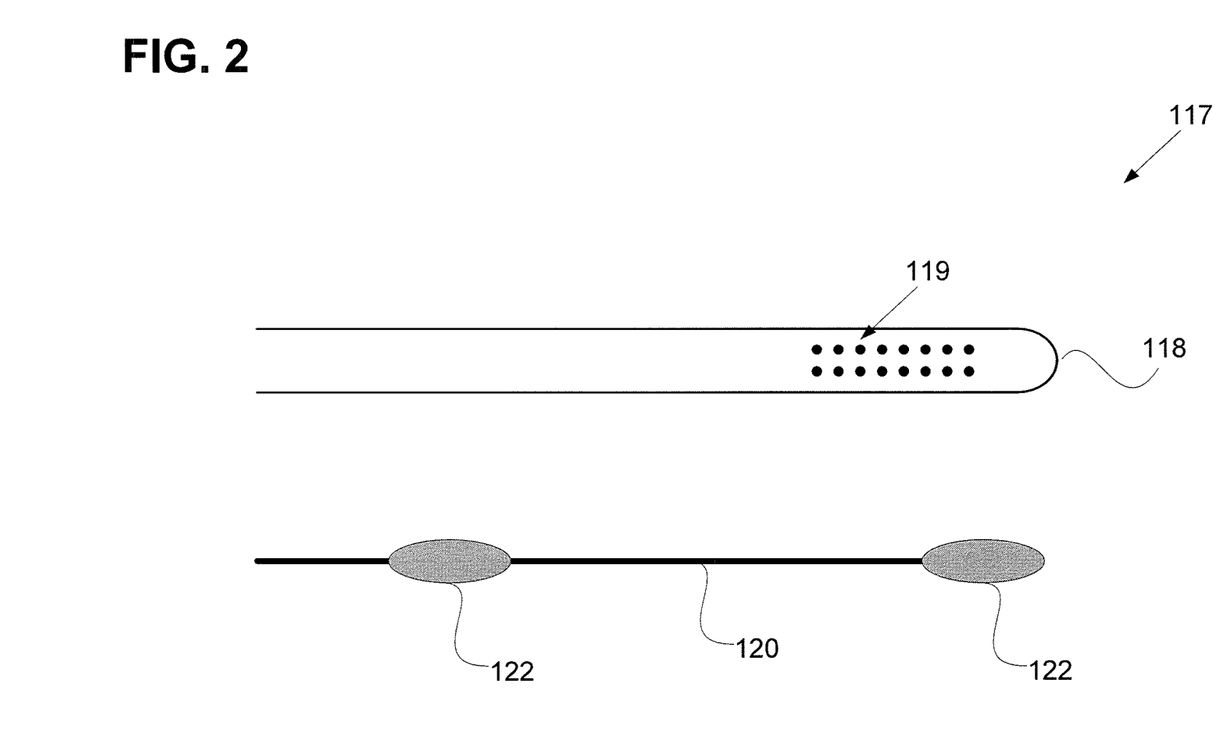
FIG. 2 shows schematic of drainage catheter and the guidewire with miniature piezoelectric sensors.

FIG. 2 is an expanded view of the drainage catheter 117 of the system, which can comprise a sheath portion 118 and a guidewire portion 120. The sheath portion can comprise a flexible material and can include one or more drainage ports 119 to facilitate the removal of bodily fluids or tissues through the catheter. The guidewire portion 120 can be insertable into the sheath portion 118 for steering the catheter to the target region in tissue. The drainage catheter can further include one or more piezoelectric (PZT) sensors 122 disposed along the guidewire portion 120. The embodiment of FIG. 2 shows 2 PZT sensors, but it should be understood that any number of PZT sensors can be implemented. For example, some embodiments utilize a single PZT sensor. The PZT sensors of the catheter can be configured to measure ultrasound pulse waveforms from individual elements of the therapy transducer 114 to extract time delays between waveforms transmitted by the therapy transducer. The time delays can then be used by the system for aberration correction.

In addition, the PZT sensors can also be used to monitor the initiation and maintenance of cavitation, which is an indication of successful histotripsy therapy and can be monitored as increased acoustic emission from the cavitation site. As the attenuation caused by the skullcap can vary across patients, such real-time cavitation detection can be used to identify the power needed to initiate cavitation for an individual patient.

Software and hardware can be configured to automatically control the pulse transmission from each element of the therapy transducer sequentially and to collect and store the signals from the PZT sensors. With only a few microseconds necessary to transmit a single pulse from one element at one time and ~100 μs for the ultrasound to travel from the element to the hydrophone, the entire data acquisition can be accomplished rapidly within a second using the automatic package.

Histotripsy Service Tool and Electronic Controller

Histotripsy Service Tool is software that can be run on any PC or computing system (e.g., electronic controller) and may be used for controlling the system. The Histotripsy Service Tool can start/stop the therapy with the therapy transducer, set and read the level of high voltage, therapy parameters (PRF, number of cycles, duty ratio, channel enabled and delay, etc.), and set and read other service and maintenance related items. The Histotripsy Service tool and Electronic Controller can be configured to set/read working parameters, start/stop the therapy, etc. It can use internal flash memory or other electronic storage media to store all the parameters. The Histotripsy Service Tool and Electronic Controller can communicate to the FPGA 108 all driving parameters that are necessary to generate complex pulsing. They can also communicate using serial communication or other electronic communication to the high voltage controller and power supply 110 where it can set/read the proper level of driving voltage.

The Histotripsy Service Tool and the Electronic controller can be coupled to the therapy transducer and the PZT sensors of the drainage catheter to use feedback from the drainage catheter during transcranial Histotripsy therapy. When ultrasound pulses propagate through a human skullcap, an aberration effect results in the peak negative pressure of the ultrasound pulses being reduced. In some experiments, the aberration effect of the skullcap has been shown to reduce the peak negative pressure to approximately 20% or less of the free-field condition of the pulses.

In one embodiment, the PZT sensors of the drainage catheter can measure the ultrasound pulse signal from each transducer element of the therapy transducer, and the Histotripsy Service Tool and the Electronic control can use these measurements and execute and aberration correction algorithm to adjust the timing of electrical pulses to each transducer element to correct for the aberration effect. The software and hardware can then automatically control the pulse transmission from each element sequentially and collect and store the measured signals. With only a few microseconds necessary to transmit a single pulse from one element at one time and ~100 µs for the ultrasound to travel from each element to the PZT sensors, the entire data acquisition can be accomplished within a second using the proposed automatic package.

Figure 3:
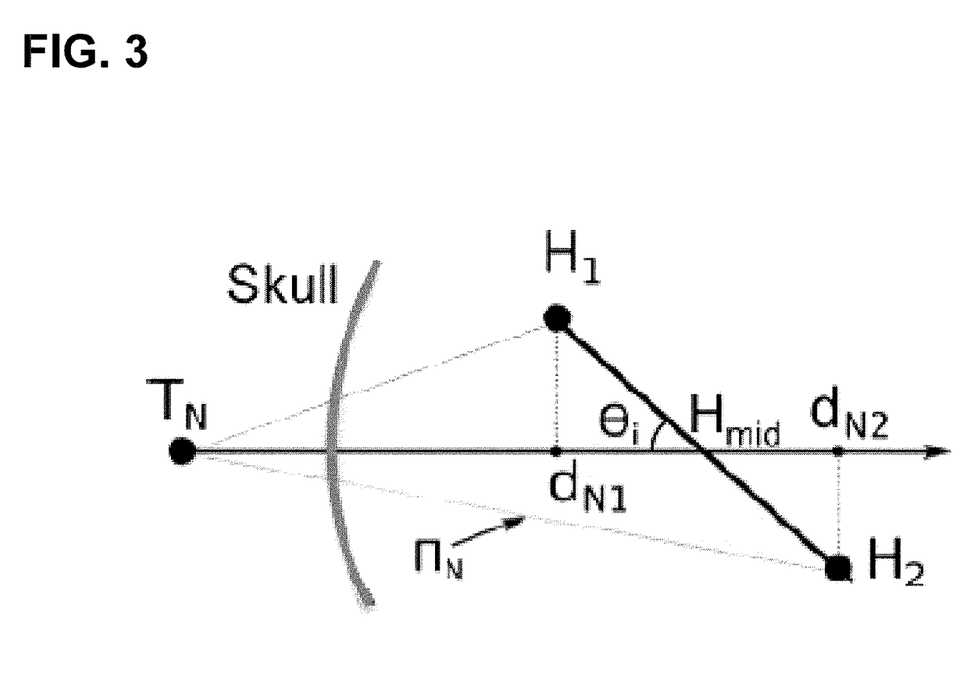
FIG. 3 illustrates the ray tracing algorithm to correct aberration of ultrasound pulses propagating through the skullcap in order to achieve focusing of histotripsy therapy through the skullcap.

An aberration correction algorithm based on ray-tracing is configured to process the measured signal from the PZT sensors to achieve precise focusing and electrical or mechanical focal steering of the therapy transducer through the skullcap. In the specific embodiment described below, the system can include two or more PZT sensors. The algorithm contains three steps, and is illustrated in FIG. 3. The steps are as follows: 1) Using the known locations of two or more PZT sensors within the catheter ($H_1$, $H_2$) and the emitting transducer element ($T_N$) of the therapy transducer, a plane, $\Pi_N$, is defined onto which the travel direction of the rays are restricted. $H_1$ and $H_2$ are assumed to be far enough from $T_N$ that the emitted signals from each individual element are effectively traveling as plane waves. The propagation time ($t_1$ and $t_2$) for the ultrasound to travel from $T_N$ to $H_1$ and $H_2$ can be calculated based on the time period between the signal arrival at the PZT sensor and its transmission from the transducer element. Using $\Delta t = t_1 - t_2$, the distance between $d_{N1}$ and $d_{N2}$ is calculated as $dist(d_{N1} - d_{N2}) = c_{tissue} * \Delta t$, where $d_{N1}$ and $d_{N2}$ are the projections of $H_1$ and $H_2$ onto the ray from $T_N$ to the midpoint of the two sensors, $H_{mid}$. The travel direction $\theta_i$ and the time of travel of the wave from $T_N$ to $H_{mid}$ can then be calculated. 2) Knowing $\theta_i$, a plane orthogonal to this wave propagation, $\Pi_{orth}$, can be defined and centered at the $H_{mid}$. Then assuming plane wave propagation, the requisite time delay of each transducer element can be calculated for a given focal location, $f_n$, by calculating the stand-off distance, $d_x$, between $\Pi_{orth}$ and $f_n$, and plugging into the equation $T(f_n) = t_{mid} + d_x/c_{tissue}$. 3) Based on the time delay calculated for all steering locations within the treatment volume, a steering pattern can be generated in the software. The software can be configured to control steering parameters as well as cavitation monitoring, and can incorporate the aberration correction algorithm to automatically collect and process the PZT sensor signals and generate adjusted steering patterns.

In one embodiment, and aberration correction algorithm based on time delays is used to achieve precise focusing and electrical or mechanical focal steering of the therapy transducer through the skullcap. In the specific embodiment described immediately below, a single PZT sensor can be used. According to this embodiment, the algorithm comprises determining a propagation time for the ultrasound pulses to travel from each of the plurality of transducer elements of the therapy transducer to the piezoelectric sensor, calculating a time delay of the propagation time between each of the plurality of transducer elements and a reference element of the therapy transducer, and adjusting the transmission of ultrasound pulses from the plurality of transducer elements based on the calculated time delays.

One limitation of ultrasound transcranial therapy is overheating to the skullcap. To address this issue, a number of strategies may be employed in addition to parameter optimization. The order in which certain elements are fired can be alternated to reduce the local heating caused by individual elements. Heat may also be reduced by using cold water as the ultrasound coupling medium to the skullcap.

Figure 4:
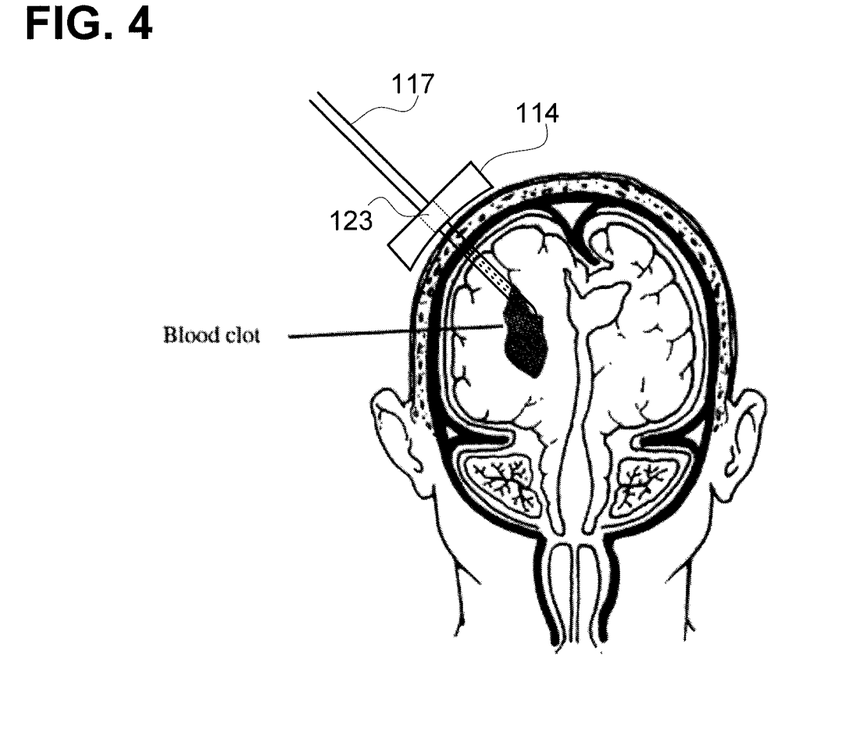
FIGS. 4-5 illustrate one embodiment and method for treating brain tissue with Histotripsy ultrasound therapy.
Figure 5:
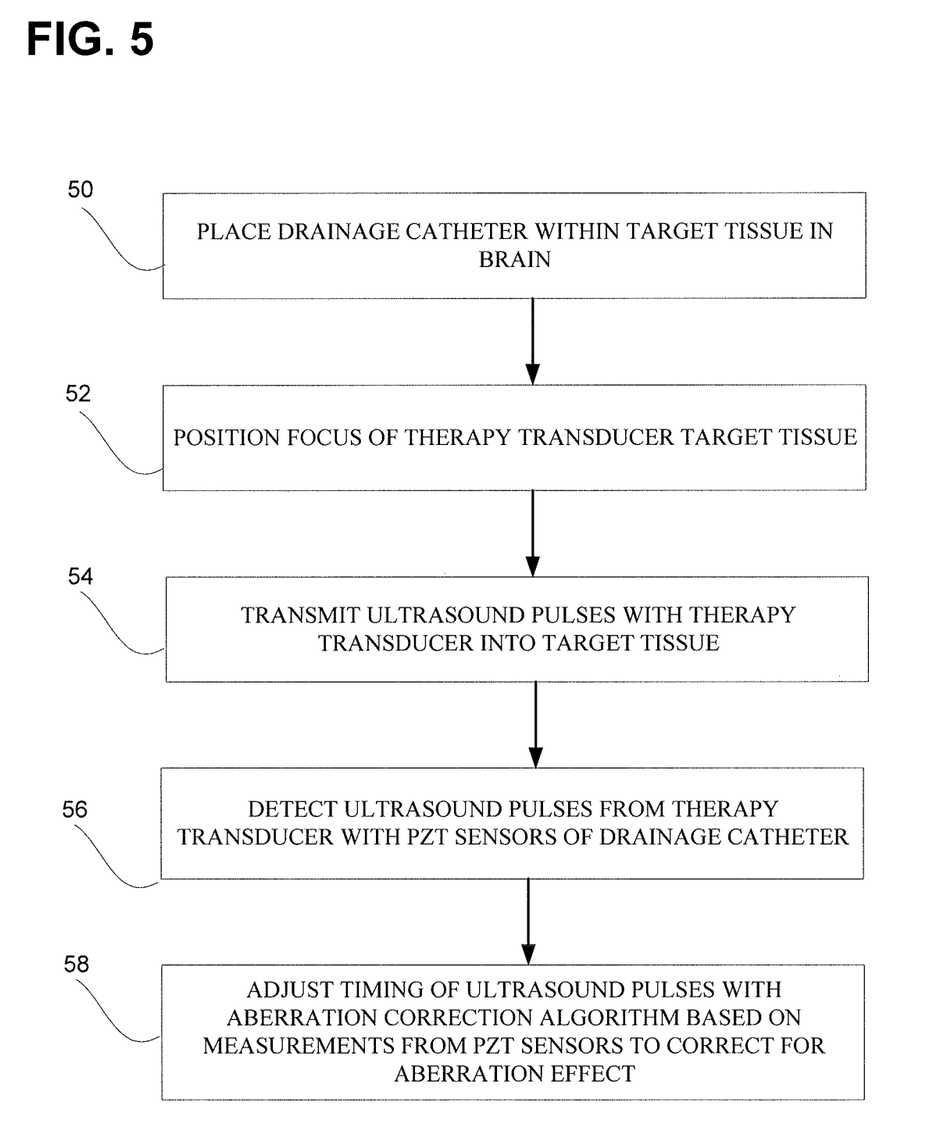

FIGS. 4-5 illustrate one embodiment and method for treating brain tissue with Histotripsy ultrasound therapy. FIG. 4 illustrates a therapy transducer 114 positioned adjacent to a skullcap of a patient, and a drainage catheter 117 positioned partially inside the brain of the patient such that drainage ports of the catheter are positioned within or adjacent to a target tissue of the brain, such as a blood clot or a brain tumor. To obtain precise focusing and focal steering, the PZT sensors in the catheter can be placed close to the geometrical focus of the transducer. In one embodiment, the therapy transducer 114 can include a hole 123 to facilitate catheter insertion through the transducer array. A catheter holder can be screwed into the hole, with scale markings on the catheter, which allows the operator to know the precise position of the catheter tip based on the insertion position, angle, and distance.

First, referring to step 50 of FIG. 5 and also to FIG. 4, the drainage catheter 117 can be inserted through the skullcap of the patient and placed within or adjacent to the target tissue in the brain. Next, referring to step 52 of FIG. 5 and also to FIG. 4, a focus of the therapy transducer 114 can be positioned on the target tissue. The therapy transducer itself can be acoustically coupled to the skull of the patient. Next, referring to step 54 of FIG. 5, ultrasound pulses can be transmitted from the therapy transducer into the target tissue. At step 56 of FIG. 5, PZT sensors of the drainage catheter can detect or measure ultrasound pulses from the therapy transducer. Finally, at step 58 of FIG. 5, the software and electronic controller of the system can adjust timing of the ultrasound pulses with an aberration correction algorithm based on the measurements from the PZT sensors to correct for the aberration effect caused by the skullcap.

The ultrasound pulses can be configured to generate cavitation or bubble clouds within the target tissue of the brain to liquefy the target tissue. In some embodiments, the liquefied target tissue can be drained with the catheter. In further embodiments, the focus of the therapy transducer can be electronically or mechanically steered to fully liquefy the target tissue.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of transmitting ultrasound energy into a brain of a human patient, comprising the steps of:
    placing a drainage catheter within a target tissue in the brain of the human patient;
    positioning a focus of a plurality of transducer elements of a therapy transducer within the target tissue;
    transmitting ultrasound pulses from each of the plurality of transducer elements into the target tissue;
    detecting the ultrasound pulses with first and second piezoelectric sensors positioned on or in the drainage catheter; and
    adjusting the transmission of ultrasound pulses from the plurality of transducer elements with an aberration correction algorithm based on the detected ultrasound pulses to automatically correct for an aberration effect caused by the ultrasound pulses passing through a skullcap of the human patient, wherein the aberration correction algorithm further comprises:
    determining a propagation time for the ultrasound pulses to travel from each of a plurality of transducer elements of the therapy transducer to the first and second piezoelectric sensors;
    calculating a distance between each of the plurality of transducer elements of the therapy transducer and the first and second piezoelectric sensors using projections of the first and second piezoelectric sensors onto a ray from each of the plurality of transducer elements to a midpoint of the first and second piezoelectric sensors;
    calculating a travel direction and a time of travel of the ultrasound pulses from each of the plurality of transducer elements to the midpoint of the first and second piezoelectric sensors;
    calculating a stand-off distance between the focus and the midpoint for each of the plurality of transducer elements; and
    calculating a time delay of each of the plurality of transducer elements based on the distance between the first and second piezoelectric sensors, the midpoint, and the stand-off distance.

2. The method of claim 1, wherein the target tissue comprises a clot or hemorrhage.

3. The method of claim 1, wherein the target tissue comprises a brain tumor.

4. The method of claim 1, further comprising forming a bubble cloud on the target tissue with the ultrasound pulses.

5. The method of claim 1, further comprising liquefying the target tissue with the ultrasound pulses.

6. The method of claim 5, further comprising draining the liquefied target tissue from the brain with the drainage catheter.

7. The method of claim 1, wherein adjusting the transmission of ultrasound pulses from the plurality of transducer elements with the aberration correction algorithm based on the detected ultrasound pulses further comprises:
    determining a propagation time for the ultrasound pulses to travel from each of the plurality of transducer elements of the therapy transducer to the one or more piezoelectric sensors;
    calculating a time delay of the propagation time between each of the plurality of transducer elements and a reference element of the therapy transducer; and
    adjusting the transmission of ultrasound pulses from the plurality of transducer elements based on the time delay for each of the plurality of transducer elements.

8. The method of claim 1 further comprising placing the one or more piezoelectric sensors within or adjacent to the focus.

9. The method of claim 1, wherein the placing step further comprises advancing the drainage catheter through a hole of the therapy transducer.

10. The method of claim 5, further comprising electronically steering the focus to fully liquefy the target tissue.

11. The method of claim 5, further comprising mechanically steering the focus to fully liquefy the target tissue.

12. An ultrasound system configured to treat a target tissue in a brain of a human patient, comprising:
    a pulse generator and an amplifier;
    an ultrasound therapy transducer coupled to the pulse generator and having a plurality of transducer elements configured to transmit ultrasound pulses through a skullcap of the human patient towards a focal point within the target tissue in the brain to generate cavitation;
    a drainage catheter comprising first and second piezoelectric sensors, the drainage catheter adapted to be placed within the brain near the focal point to measure the ultrasound pulses;
    an electronic controller coupled to the pulse generator, the ultrasound therapy transducer, and the piezoelectric sensors of the drainage catheter, the electronic controller being configured to control transmission of the ultrasound pulses and adjust the transmission of ultrasound pulses from each of the plurality of transducer elements by executing an aberration correction algorithm based on the ultrasound pulses detected by the drainage catheter to automatically correct for an aberration effect caused by the ultrasound pulses passing through the skullcap of the human patient, wherein the aberration correction algorithm comprises:
    determining a propagation time for the ultrasound pulses to travel from each of the plurality of transducer elements of the therapy transducer to the first and second piezoelectric sensors;
    calculating a distance between each of the plurality of transducer elements of the therapy transducer and the first and second piezoelectric sensors using projections of the first and second piezoelectric sensors onto a ray from each of the plurality of transducer elements to a midpoint of the first and second piezoelectric sensors;
    calculating a travel direction and a time of travel of the ultrasound pulses from each of the plurality of transducer elements to the midpoint of the first and second piezoelectric sensors;
    calculating a stand-off distance between the focus and the midpoint for each of the plurality of transducer elements; and calculating a time delay of each of the plurality of transducer elements based on the distance between the first and second piezoelectric sensors, the midpoint, and the stand-off distance.

13. The ultrasound system of claim 12, wherein the ultrasound therapy transducer is configured to transmit histotripsy therapy pulses to generate cavitation to liquefy the target tissue within the brain of the human patient.

14. The ultrasound system of claim 13, the drainage catheter including drainage ports configured to drain the liquefied target tissue from the human patient.

15. The ultrasound system of claim 12, wherein the one or more piezoelectric sensors comprises exactly one piezoelectric sensor.

16. The ultrasound system of claim 15, wherein the aberration correction algorithm comprises:
   determining a propagation time for the ultrasound pulses to travel from each of the plurality of transducer elements of the therapy transducer to piezoelectric sensor;
   calculating a time delay of the propagation time between each of the plurality of transducer elements and a reference element of the therapy transducer; and
   adjusting the transmission of ultrasound pulses from the plurality of transducer elements based on the time delay for each of the plurality of transducer elements.

17. The ultrasound system of claim 12, wherein the therapy transducer comprises a hole through which the drainage catheter is configured to be advanced into the brain of the human patient.

* * * * *